(12) United States Patent
Viglietta

(10) Patent No.: US 10,994,003 B2
(45) Date of Patent: *May 4, 2021

(54) DIMETHYL FUMARATE AND VACCINATION REGIMENS

(71) Applicant: Biogen MA Inc., Cambridge, MA (US)

(72) Inventor: Vissia Viglietta, Boston, MA (US)

(73) Assignee: Biogen MA Inc., Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/729,710

(22) Filed: Dec. 30, 2019

(65) Prior Publication Data

US 2020/0360501 A1 Nov. 19, 2020

Related U.S. Application Data

(63) Continuation of application No. 16/391,583, filed on Apr. 23, 2019, now Pat. No. 10,555,993, which is a continuation of application No. 15/125,612, filed as application No. PCT/US2015/020470 on Mar. 13, 2015, now Pat. No. 10,391,160.

(60) Provisional application No. 61/953,259, filed on Mar. 14, 2014.

(51) Int. Cl.
*A61K 39/09* (2006.01)
*A61K 39/05* (2006.01)
*A61K 31/225* (2006.01)
*A61K 39/00* (2006.01)

(52) U.S. Cl.
CPC .......... *A61K 39/092* (2013.01); *A61K 31/225* (2013.01); *A61K 39/05* (2013.01); *A61K 2039/545* (2013.01); *A61K 2039/6081* (2013.01)

(58) Field of Classification Search
CPC .... A61K 39/092; A61K 39/05; A61K 31/225; A61K 2039/545; A61K 2039/6081; A61P 37/04; A61P 31/00; A61P 25/28
See application file for complete search history.

(56) References Cited

U.S. PATENT DOCUMENTS

| | | |
|---|---|---|
| 6,509,376 B1 | 1/2003 | Joshi et al. |
| 9,326,947 B1 | 5/2016 | Dyakonov et al. |
| 9,326,965 B2 | 5/2016 | Dyakonov et al. |
| 9,511,043 B2 | 12/2016 | Dyakonov et al. |
| 9,517,209 B2 | 12/2016 | Dyakonov et al. |
| 9,566,259 B1 | 2/2017 | Vaughn et al. |
| 9,636,318 B2 | 5/2017 | Vaughn et al. |
| 9,636,319 B1 | 5/2017 | Vaughn et al. |
| 9,814,691 B2 | 11/2017 | Dyakonov et al. |
| 9,814,692 B2 | 11/2017 | Vaughn et al. |
| 9,820,960 B2 | 11/2017 | Dyakonov et al. |
| 9,820,961 B2 | 11/2017 | Vaughn et al. |
| 10,098,863 B2 | 10/2018 | Vaughn et al. |
| 10,391,160 B2 | 8/2019 | Viglietta |
| 10,555,993 B2 | 2/2020 | Viglietta |
| 2013/0216615 A1 | 8/2013 | Goldman et al. |
| 2018/0055804 A1 | 3/2018 | Vaughn et al. |
| 2018/0055806 A1 | 3/2018 | Dyakonov et al. |
| 2018/0278918 A1 | 9/2018 | Peri et al. |

FOREIGN PATENT DOCUMENTS

| | | |
|---|---|---|
| WO | WO 2016/057133 A1 | 4/1916 |
| WO | WO 2006/037342 A2 | 4/2006 |
| WO | WO 2015/130998 A1 | 9/2015 |
| WO | WO 2015/138917 A1 | 9/2015 |
| WO | WO 2016/081355 A1 | 5/2016 |
| WO | WO 2017/040272 A1 | 3/2017 |
| WO | WO 2017/151184 A1 | 9/2017 |

OTHER PUBLICATIONS

Appeal Brief under 37 C.F.R. § 41.37 filed Jan. 23, 2020 for U.S. Appl. No. 16/043,641; 21 pages.
Appellant's Reply Brief filed May 18, 2020 for U.S. Appl. No. 16/043,641; 11 pages.
Applicant-Initiated Interview Summary dated Jul. 21, 2020 for U.S. Appl. No. 15/647,016; 10 pages.
Cahill et al., 2010, "Immunization in Patients With Multiple Sclerosis", Neurol. Bull. 2: 17-21.
Decision on Petition dated Jul. 8, 2020 for U.S. Appl. No. 16/043,641; 2 pages.
Declaration Under 37 C.F.R.§ 1.132 of Mark Novas filed Mar. 25, 2020 for U.S. Appl. No. 16/173,723; 9 pages.
Declaration Under 37 C.F.R.§ 1.132 of Mark Novas filed Jul. 20, 2020 for U.S. Appl. No. 15/647,016; 25 pages.
Examiner's Answer dated Mar. 18, 2020 for U.S. Appl. No. 16/043,641; 12 pages.
Extended European Search Report dated Apr. 9, 2020 for EP Application No. 19199534.9; 7 pages.
Notice of Non-Compliant Appeal Brief dated Feb. 3, 2020 for U.S. Appl. No. 16/043,641; 2 pages.
Office Action dated Jan. 23, 2020 for U.S. Appl. No. 15/527,252; 18 pages.
Office Action dated Jun. 10, 2020 for U.S. Appl. No. 16/173,723; 12 pages.
Office Action dated Jun. 24, 2020 for U.S. Appl. No. 15/647,016; 18 pages.
Response to Final Office Action filed Mar. 25, 2020 for U.S. Appl. No. 16/173,723; 14 pages.
Response to Final Office Action filed Jul. 20, 2020 for U.S. Appl. No. 15/647,016; 13 pages.
Response to Notice of Non-Compliant Appeal Brief filed Feb. 3, 2020 for U.S. Appl. No. 16/043,641; 6 pages.
Abu-Shakra, 2009, "Safety of vaccination of patients with systemic lupus erythematosus", Lupus, 18:1205-1208.

(Continued)

*Primary Examiner* — Snigdha Maewall
(74) *Attorney, Agent, or Firm* — Jones Day

(57) ABSTRACT

Provided herein is a method of treating or preventing a disease or disorder (e.g., MS) in a subject in need thereof, comprising (a) administering to the subject a first dose of a pharmaceutical composition comprising a fumarate agent (e.g., DMF) for a first dosing period; (b) administering a vaccine; and (c) administering to the subject a second dose of the pharmaceutical composition for a second dosing period.

26 Claims, No Drawings

(56) References Cited

OTHER PUBLICATIONS

Auriel et al., 2012, "Seasonal and H1N1v Influenza Vaccines in MS: Safety and Compliance," Journal of Neurological Science., 314(1-2):102-103.
Hehn et al., 2017, "Immune response to vaccines is maintained in patients treated with dimethyl fumarate", Neurol. Neuroimmunol. Neuroinflamm., 5(1):e409.
Highlights of Prescribing Information (with Full Prescribing Information) AUBAGIO™ (teriflunomide) tablets, for oral administration; revised Sep. 2012, 27 pages.
Highlights of Prescribing Information (with Full Prescribing Information) AVONEX™ (interferon beta-1a) injection, for intramuscular injection; revised Mar. 2013, 19 pages.
Highlights of Prescribing Information (with Full Prescribing Information) BETASERON™ (interferon beta-1b) for injection, for subcutaneous use; revised Jan. 2014, 30 pages.
Highlights of Prescribing Information (with Full Prescribing Information) COPAXONE™ (glatiramer acetate injection) solution for subcutaneous injection; revised Aug. 2012, 22 pages.
Highlights of Prescribing Information (with Full Prescribing Information) EXTAVIA™ (Interferon beta-1b) Kit for subcutaneous use; revised Jul. 2009, 21 pages.
Highlights of Prescribing Information (with Full Prescribing Information) GILENYA™ (fingolimod) capsules; revised May 2012, 17 pages.
Highlights of Prescribing Information (with Full Prescribing Information) GILENYA™ (fingolimod) capsules; revised Apr. 2014, 23 pages.
Highlights of Prescribing Information (with Full Prescribing Information), LEMTRADA™ (alemtuzumab) injection, for intravenous use; revised Nov. 2014, 36 pages.
Highlights of Prescribing Information (with Full Prescribing Information), LEMTRADA™, (alemtuzumab) injection, for intravenous use; revised Dec. 2017, 29 pages.
Highlights of Prescribing Information (with Full Prescribing Information), TECFIDERA™, (dimethyl fumarate) delayed-release capsules, for oral use; revised Mar. 2013; 15 pages.
Highlights of Prescribing Information (with Full Prescribing Information), TYSABRI™ (natalizumab) injection, for intravenous use; revised Dec. 2013, 34 pages.
International Preliminary Report on Patentability dated Sep. 22, 2016 for International Patent Application No. PCT/US2015/020470; 7 pages.
International Search Report dated Jun. 3, 2015 for International Application PCT/US2015/020470; 3 pages.
Label, NOVANTRONE™, mitoXANTRONE for injection concentrate; Mar. 2012, 37 pages.
Label, REBIF™ (interferon beta-1a) Description; Apr. 2013, 31 pages.
Lehmann et al., 2007, "Dimethylfumarate Induces Immunosuppression via Glutathione Depletion and Subsequent Induction of Heme Oxygenase 1," J. of Invest. Dermatol., 127, (4):835-845.
Mrowietz et al., 1999, "Treatment of Severe Psoriasis with Fumaric Acid Esters: Scientific Background and Guidelines for Therapeutic Use," British J. of Dermatol., 141(3):424-29.
Olberg et al., 2014, "Immunotherapies Influence the Influenza Vaccination Response in Multiple Sclerosis Patients: An Explorative Study," Multiple Sclerosis, 20(8):1074-80.
Office Action dated Jun. 4, 2018 in U.S. Appl. No. 15/527,252; 11 pages.
Amendment and Response dated Aug. 31, 2018, filed in U.S. Appl. No. 15/527,252; 15 pages.
Office Action dated Nov. 8, 2018 in U.S. Appl. No. 15/527,252; 15 pages.
Office Action dated Jan. 26, 2018 in U.S. Appl. No. 15/647,016; 12 pages.
Amendment and Response dated Jul. 26, 2018, filed in U.S. Appl. No. 15/647,016; 14 pages.
Office Action dated Nov. 8, 2018 in U.S. Appl. No. 15/647,016; 15 pages.
Office Action dated Nov. 24, 2017 in U.S. Appl. No. 15/647,036; 6 pages.
Amendment and Response dated Feb. 23, 2018, filed in U.S. Appl. No. 15/647,036; 14 pages.
Office Action dated Apr. 30, 2018 in U.S. Appl. No. 15/647,036; 9 pages.
Office Action dated Oct. 23, 2018 in U.S. Appl. No. 16/043,641; 9 pages.
Response to Office Action under 37 C.F.R. § 1.11 dated Jan. 22, 2019, filed in U.S. Appl. No. 16/043,641; 16 pages.
Supplemental Response to Office Action and Amendment under 37 C.F.R. § 1.111 dated Feb. 28, 2019, filed in U.S. Appl. No. 16/043,641; 23 pages.
Package Insert, NOVANTRONE™, mitoxantrone, for injection concentrate, 2000, 35 pages.
Polman et al., 2010, "Diagnostic Criteria for Multiple Sclerosis: 2010 Revisions to the McDonald Criteria," Ann. Neurol., 69(2):292-02.
Schwid et al., 2005, "Enhanced Benefit of Increasing Interferon Beta-1a Dose and Frequency in Relapsing Multiple Sclerosis: The Evidence Study," Arch. Neurol., 62(5):785-92.
Shoenfeld, 2009, "Infections, vaccines and autoimmunity", Lupus, 18:1127-1128.
Summary of Product Characteristics, including Annex I-III, TECFIDERA™, capsule, for oral use, Feb. 26, 2014; European Medicines Agency, 46 pages.
Summary of Product Characteristics, TECFIDERA™, Date of latest renewal: Sep. 20, 2018. [retrieved Mar. 15, 2019] Retrieved from the internet <URL: https://www.ema.europa.eu/en/documents/product-information/tecfidera-epar-product-information_en.pdf>, 37 pages.
"Vaccination Response in Tecfidera-Treated Versus Interferon-Treated Participants with Relapsing Forms of Multiple Sclerosis," dated Mar. 25 2014, ClinicalTrials.gov; [on-line], [retrieved on May 15, 2015], Retrieved from the Internet: <URL:https://www.clinicaltrials.gov/ct2/show/study/NCT02097849>; 11 pages.
Written Opinion of the International Searching Authority dated Jun. 3, 2015 for International Application PCT/US2015/020470; 6 pages.
Office Action dated Mar. 25, 2019 in U.S. Appl. No. 16/043,641; 10 pages.
Interview Summary dated Aug. 30, 2019 in U.S. Appl. No. 16/043,641; 5 pages.
Interview Summary and Supplemental Amendment dated Aug. 30, 2019 in U.S. Appl. No. 15/647,016; 20 pages.
Office Action dated Jun. 17, 2019 in U.S. Appl. No. 16/043,641; 12 pages.
Office Action dated Feb. 7, 2019 in U.S. Appl. No. 16/173,723; 7 pages.
Response to Final Office Action Under 37 C.F.R.§ 1.114 dated May 8, 2019 in U.S. Appl. No. 16/043,641 (with Declaration of Ellen Cahir-McFarland, Ph.D. Under 37 C.F.R. § 1.132); 368 pages.
Response to Non-Final Office Action dated Aug. 14, 2019 in U.S. Appl. No. 16/043,641 (with Declaration Under 37 C.F.R. § 1.130(a) and 1.130(b) by Mark Novas, M.D.); 260 pages.
Response to Non-Final Office Action Under 37 C.F.R. § 1.114 (c) dated Aug. 7, 2019 in U.S. Appl. No. 16/173,723; 13 pages.
Response to Final Office Action dated Aug. 5, 2019, filed in U.S. Appl. No. 15/647,016 (with Declaration Under 37 C.F.R. § 1.130(a) and 1.130(b) by Mark Novas, M.D. and Declaration Under 37 C.F.R. § 1.132 by Ellen Cahir-McFarland, Ph.D. ); 653 pages.
Applicant-Initiated Interview Summary (PTOL-413) dated Sep. 5, 2019 in U.S. Appl. No. 16/043,641; (with Agenda for Interview; Timeline of Events, Dimethyl Fumarate (Tecfidera) Criteria for Use; and Dimethyl Fumarate (Tecfidera) National Drug Monograph May 2013); 6 pages.
Applicant-Initiated Interview Summary (PTOL-413) dated Sep. 6, 2019 in U.S. Appl. No. 15/647,016; 4 pages.
Response to Examiner's Interview Summary dated Sep. 23, 2019, of U.S. Appl. No. 15/647,016; 3 pages.
Argument Accompanying Pre-Appeal Brief Request for Review dated Oct. 7, 2019, of U.S. Appl. No. 16/043,641; 5 pages.
Office Action dated Oct. 30, 2019 in U.S. Appl. No. 15/647,016; 17 pages.

(56) References Cited

OTHER PUBLICATIONS

Office Action dated Sep. 27, 2019 in U.S. Appl. No. 16/043,641; 12 pages.
Office Action dated Sep. 27, 2019 in U.S. Appl. No. 16/173,723; 11 pages.
Response to Final Office Action dated Dec. 6, 2019 of U.S. Appl. No. 15/527,252; 7 pages.
Response to Non-final Office Action filed Mar. 27, 2020 for U.S. Appl. No. 15/647,016; 17 pages.
Declaration Under 37 C.F.R.§ 1.132 of Mark Novas filed Mar. 27, 2020 for U.S. Appl. No. 15/647,016; 9 pages.
Applicant-Initiated Interview Summary (PTOL-413) dated Mar. 13, 2018 for U.S. Appl. No. 15/647,036; 3 pages.
Response to Examiner's Interview Summary dated Mar. 30, 2018, for U.S. Appl. No. 15/647,036; 2 pages.
Applicant-Initiated Interview Summary dated Jul. 12, 2020 for U.S. Appl. No. 16/173,723; 2 pages.
Response to Non-final Office Action filed Aug. 25, 2020 for U.S. Appl. No. 16/173,723; 13 pages.
Declaration Under 37 C.F.R.§ 1.132 of Mark Novas filed Aug. 25, 2020 for U.S. Appl. No. 16/173,723; 25 pages.
Office Action dated Nov. 24, 2020 for U.S. Appl. No. 17/071,740; 24 pages.
Response to Non-final Office Action filed Dec. 2, 2020 for U.S. Appl. No. 16/936,398; 15 pages.
Notice of Allowance dated Jan. 13, 2021 for U.S. Appl. No. 16/936,398; 9 pages.
Applicant-Initiated Interview Summary dated Feb. 11, 2021 for U.S. Appl. No. 17/071,740, 2 pages.
Interview Summary dated Feb. 24, 2019 for U.S. Appl. No. 16/043,641; 2 pages.
Interview Summary dated Jun. 14, 2019 for U.S. Appl. No. 16/043,641; 3 pages.
Record of Oral Hearing held Oct. 1, 2020 for U.S. Appl. No. 16/043,641, Transcript mailed Oct. 16, 2020; 14 pages.
Declaration Under 37 C.F.R. § 1.132 of Ellen Cahir-McFarland filed Aug. 7, 2019 for U.S. Appl. No. 16/173,723; 12 pages.
Notice of Allowance dated Sep. 30, 2020 for U.S. Appl. No. 16/173,723; 7 pages.
Office Action dated Sep. 2, 2020 for U.S. Appl. No. 16/936,398; 22 pages.

DIMETHYL FUMARATE AND VACCINATION REGIMENS

This application is a continuation of U.S. patent application Ser. No. 16/391,583, filed Apr. 23, 2019, which is a continuation of U.S. patent application Ser. No. 15/125,612, which is a national stage application of International Patent Application No. PCT/US2015/020470, filed Mar. 13, 2015, which claims the benefit of U.S. provisional application No. 61/953,259 filed Mar. 14, 2014, each of which is incorporated by reference herein in its entirety.

1. FIELD OF INVENTION

The present invention generally relates to methods of treating or preventing a neurological disease or disorder (e.g., multiple sclerosis) in a subject who receiver a vaccine.

2. BACKGROUND OF THE INVENTION

TECFIDERA™ has been approved by the U.S. Food and Drug Administration for the treatment of patients with relapsing forms of multiple sclerosis (MS). TECFIDERA™ contains dimethyl fumarate (DMF), which has the following structure:

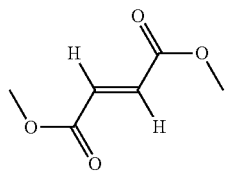

The starting dose for TECFIDERA™ is 120 mg twice a day orally. After 7 days, the dose is to be increased to the maintenance dose of 240 mg twice a day orally. TECFIDERA™ can be taken with or without food.

Vaccines are an important class of medications that are frequently used for treating or preventing various diseases, such as infectious diseases. Patients having MS can receive one or more vaccines prior to or during treatments with DMF. One objective of the present invention is to provide a method of treating or preventing multiple sclerosis in patients who receive a vaccine.

3. BRIEF SUMMARY OF THE INVENTION

In some embodiments, the invention provides a method of treating or preventing a disease or disorder (e.g., MS) in a subject in need thereof, comprising
(a) administering to the subject a first dose of a pharmaceutical composition for a first dosing period, wherein the pharmaceutical composition comprises a fumarate agent selected from the group consisting of monomethyl fumarate ("MMF"), a compound that metabolizes into monomethyl fumarate in vivo, a deuterated analog thereof, a pharmaceutically acceptable salt thereof, and a combination thereof;
(b) administering a vaccine to the subject; and
(c) administering to the subject a second dose of the pharmaceutical composition for a second dosing period, wherein the second dosing period is after the first dosing period, stopping administration of the pharmaceutical composition (i.e., the second dose can be null). In some embodiments, the subject is administered the same amount of fumarate agent as in the first dosing period after the second dosing period.

In some embodiments, the invention provides a method of treating or preventing a disease or disorder (e.g., MS) in a subject in need thereof, comprising
(a) administering to the subject a first dose of a pharmaceutical composition for a first dosing period, wherein the pharmaceutical composition comprises a fumarate agent selected from the group consisting of monomethyl fumarate, a compound that metabolizes into monomethyl fumarate in viva, a deuterated analog thereof, a pharmaceutically acceptable salt thereof, and a combination thereof, and wherein the subject receives a vaccine;
(b) determining an immune response of the subject to the vaccine before the end of the first dosing period; and
(c) adjusting the first dose to a second dose of the pharmaceutical composition, which includes stopping administration of the pharmaceutical composition (i.e., the second dose can be null), based on the immune response determined in step (b).

In some embodiments, the invention provides a method of treating or preventing a disease or disorder (e.g., MS) in a subject in need thereof, comprising
(a) administering to the subject a first dose of a pharmaceutical composition for a first dosing period, wherein the pharmaceutical composition comprises a fumarate agent selected from the group consisting of monomethyl fumarate, a compound that metabolizes into monomethyl fumarate in vivo, a deuterated analog thereof, a pharmaceutically acceptable salt thereof, and a combination thereof, and wherein the subject receives a vaccine;
(b) determining an immune response of the subject to the vaccine before the end of the first dosing period; and
(c) administering to the subject a second dose of the pharmaceutical composition for a second dosing period. In some embodiments, the second dose is equal to or less than the first dose. In some embodiments, the subject is administered the same amount of fumarate agent as in the first dosing period after the second dosing period.

In some embodiments, the first or second dose of the pharmaceutical composition contains a therapeutically effective amount of the fumarate agent. In some embodiments, the fumarate agent comprises MMF, DMF, or a combination thereof. In some embodiments, the fumarate agent comprises DMF. In some embodiments, the only active ingredient in the pharmaceutical composition is DMF. In some embodiments, the first dose is a daily amount of about 480 mg dimethyl fumarate administered twice per day (BID). In some embodiments, the second dose is about 0 mg to about 480 mg fumarate agent (e.g., DMF).

In some embodiments, the step of determining the immune response comprises obtaining serum antibody (e.g., IgG or IgM) levels in the subject induced by the vaccine post-immunization (e.g., 4 weeks after immunization), obtaining the serum antibody (e.g., IgG or IgM) levels in the subject pre-immunization, and comparing the serum antibody levels in the subject pre- and post-immunization. In some embodiments, the serum antibody is IgG against tetanus diphtheria toxoids, keyhole limpet hemocyanin, or pneumovax-23, and the scrum IgG level in the subject increases less than 4-fold (e.g., less than 3-fold or less than 2-fold) from pre-vaccination to 4 weeks after vaccination. In some embodiments, the serum IgG level in the subject increases at least 2-fold (e.g., at least 4-fold or at least 10-fold) from pre-immunization to 4 weeks after immunization.

The immune response following vaccination, e.g., as determined by the determining step, can affect the second dose. In some embodiments, the immune response of the subject to the vaccine is characterized in that the serum antibody level induced by the vaccine in the subject increases less than 4-fold (e.g., less than 3-fold or less than 2-fold) from pre-vaccination to 4 weeks after vaccination, and the second dose is about 5% to about 95% (e.g., about 10%, about 20%, about 30%, about 40%, about 50%, about 60%, about 70%, about 80%, about 90%, or any ranges thereof) of the first dose. In some embodiments, the second dose is a daily dose of about 0 to about 480 mg. In some embodiments, the immune response of the subject to the vaccine is characterized in that the serum antibody level in the subject increases at least 2-fold (e.g., at least 4-fold or at least 10-fold) from pre-immunization to 4 weeks after immunization, and the second dose is the same as the first dose.

In some embodiments, the methods described herein further comprise administering a titration dose of the pharmaceutical composition prior to the first and/or second dosing periods. In some embodiments, the titration dose is administered to the subject for at least 7 days prior to beginning the first and/or second dosing period. In some embodiments, the fumarate agent is DMF and the titration dose is a daily dose of about 240 mg DMF administered BID for 7 consecutive days. In some embodiments, the fumarate agent is DMF and the titration dose is a daily dose of 360 mg DMF administered three times a day.

In some embodiments, the invention also provides a method of treating or preventing a disease or disorder (e.g., MS) in a subject who receives a vaccine, comprising screening a plurality of doses of a pharmaceutical composition comprising a fumarate agent selected from the group consisting of monomethyl fumarate, a compound that metabolizes into monomethyl fumarate in vivo, a deuterated analog thereof, a pharmaceutically acceptable salt thereof, and a combination thereof, by
  (1) identifying a first group of subjects and at least a second group of subjects, wherein both the first and second groups of subjects receive a vaccine, wherein the first group of subjects is treated with a first dose of the pharmaceutical composition, and the second group of subjects is treated with a second dose of the pharmaceutical composition; and
  (2) determining a lower risk dose. In some embodiments, the method further comprises administering the lower risk dose of the pharmaceutical composition to the subject. In some embodiments, the lower risk dose is determined by comparing immune responses to the vaccine between the first and second groups of subjects.

In some embodiments, the invention provides a method of treating or preventing multiple sclerosis in a subject in need thereof, comprising
  (a) determining a subject's baseline lymphocyte count prior to treatment;
  (b) administering to the subject a first dose of a pharmaceutical composition for a first dosing period, wherein the pharmaceutical composition comprises a fumarate agent selected from the group consisting of monomethyl fumarate, a compound that metabolizes into monomethyl fumarate in vivo, a deuterated analog thereof, a pharmaceutically acceptable salt thereof, and a combination thereof;
  (c) determining a subject's total lymphocyte count after the first dosing period; and
  (d) if the lymphocyte count after the first dosing period is about 90% of the baseline lymphocyte count or lower, do not administer tetanus diphtheria toxoids vaccine, keyhole limpet hemocyanin vaccine, pneumovax-23 vaccine, or any combinations thereof.

In some embodiments, the invention provides a method of treating multiple sclerosis in a human subject in need thereof comprising
  (a) administering a therapeutically effective amount of dimethyl fumarate to the subject; and
  (b) administering a vaccine to the subject.

4. DETAILED DESCRIPTION OF THE INVENTION

4.1 Definitions

As used herein, "a" or "an" means one or more unless otherwise specified.

Unless specifically stated or obvious from context, as used herein, the term "about" is understood as within a range of normal tolerance in the art, for example, within 20% of the stated value. As used herein, "about" a specific value also includes the specific value, for example, about 10% includes 10%.

As used herein, the term "DMF," or "BG00012" refers to the compound dimethyl fumarate. The term "MMF" refers to the compound, or an ionized form of, monomethyl fumarate.

Open terms such as "include," "including," "contain," "containing" and the like mean "comprising."

The term "treating" refers to administering a therapy in an amount, manner, or mode effective to improve a condition, symptom, or parameter associated with a disease or disorder.

The term "prophylaxis", the term "prophylactic treatment", or "preventing" refers to precluding a patient from getting a disorder, causing a patient to remain free of a disorder for a longer period of time, or halting the progression of a disorder, to either a statistically significant degree or to a degree detectable to one skilled in the art.

The terms "therapeutically effective dose" and "therapeutically effective amount" refer to that amount of a compound which results in prevention or delay of onset or amelioration of symptoms of a neurological disorder in a subject or an attainment of a desired biological outcome, such as reduced neurodegeneration (e.g., demyelination, axonal loss, or neuronal death) or slowing in the accumulation of physical disability (e.g., as indicated by, e.g., a reduced rate of worsening of a clinical score (e.g., Enhanced Disability Status Scale ("EDSS")) or another suitable parameter indicating disease state. Exemplary disease state parameters include the number of clinical relapses, number of T1 lesions, reduced mean number of new and total gadolinium-enhancing (Gd+) lesions on brain MRI scans, number and volume of new or newly-enlarging T2 hyperintense lesions, number of new T hypointense lesions, percentage of Gd+ lesions that convert to T1 hypointense lesions, measures of atrophy and magnetization transfer ratio, and the like).

The term "microtablet" means a compact in the form of a small (micro) tablet having a mean diameter of less than 5,000 microns (e.g., about 1,000 microns to about 3,000 microns), excluding any coating, that comprises the active ingredient(s) and one or more excipients. The active ingredient(s) and excipients can be homogeneously or heterogeneously mixed in the microtablet. In any of the embodiments described herein, the microtablets may be coated, for example, by a seal coating, an enteric coating, or a combination thereof.

As used herein, when an object (e.g., a microtablet) is said to be "coated" or have a "coating," it is to be understood that the object can be fully or partially coated by one or more coatings. Similarly, when an object (e.g., a microtablet) is said to be "encapsulated," it is to be understood that the object can be fully or partially encapsulated.

The term "subject" as used herein generally refers to human, including healthy human or a patient with certain diseases or disorders (e.g., MS).

4.2 Compounds that can be Metabolized into MMF

A compound that can be metabolized into MMF in vivo, as used herein, includes DMF. A compound that can be metabolized into MMF in vivo, as used herein, includes any such compound known in the art. For example, a compound that can be metabolized into MMF in vivo, as used herein includes, for example, any compound described in U.S. application Ser. No. 13/760,916, the content of which is incorporated herein by reference in its entirety.

Compounds that can be metabolized into MMF in vivo include compounds of Formula I:

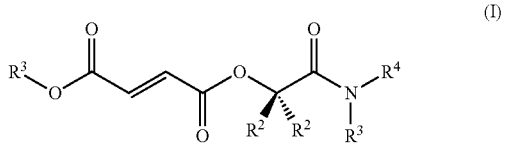

(I)

or a pharmaceutically acceptable salt thereof, wherein
$R^1$ and $R^2$ are independently chosen from hydrogen, $C_{1-6}$ alkyl, and substituted $C_{1-6}$ alkyl;
$R^3$ and $R^4$ are independently chosen from hydrogen, $C_{1-6}$ alkyl, substituted $C_{1-6}$ alkyl, $C_{1-6}$ heteroalkyl, substituted $C_{1-6}$ heteroalkyl, $C_{4-12}$ cycloalkylalkyl, substituted $C_{4-12}$ cycloalkylalkyl, $C_{7-12}$ arylalkyl, and substituted $C_{7-12}$ arylalkyl; or $R^3$ and $R^4$ together with the nitrogen to which they are bonded form a ring chosen from a $C_{5-10}$ heteroaryl, substituted $C_{5-10}$ heteroaryl, $C_{5-10}$ heterocycloalkyl, and substituted $C_{5-10}$ heterocycloalkyl; and
$R^5$ is chosen from methyl, ethyl, and $C_{3-6}$ alkyl;
wherein each substituent group is independently chosen from halogen, —OH, —CN, —CF$_3$, =O, —NO$_2$, benzyl, —C(O)NR$^{11}$$_2$, —R$^{11}$, —OR$^{11}$, —C(O)R$^{11}$, —COOR$^{11}$, and —NR$^{11}$$_2$ wherein each R$^{11}$ is independently chosen from hydrogen and $C_{1-4}$ alkyl;
with the proviso that when $R^5$ is ethyl; then $R^3$ and $R^4$ are independently chosen from hydrogen, $C_{1-6}$ alkyl, and substituted $C_{1-6}$ alkyl.

Useful examples of a compound of Formula (I) include: (N,N-diethylcarbamoyl)methyl methyl(2E)but-2-ene-1,4-dioate; methyl[N-benzylcarbamoyl]methyl(2E)but-2-ene-1,4-dioate; methyl 2-morpholin-4-yl-2-oxoethyl(2E)but-2-ene-1,4-dioate; (N-butylcarbamoyl)methyl methyl(2E)but-2-ene-1,4-dioate; [N-(2-methoxyethyl)carbamoyl]methyl methyl(2E)but-2-ene-1,4-dioate; 2-{2-[(2E)-3-(methoxycarbonyl)prop-2-enoyloxy)acetylamino}acetic acid; 4-{2-[(2E)-3-(methoxycarbonyl)prop-2-enoyloxy] acetylamino}butanoic acid; methyl(N-(1,3,4-thiadiazol-2-yl)carbamoyl)methyl(2E)but-2ene-1,4-dioate; (N,N-dimethylcarbamoyl)methyl methyl(2E)but-2-ene-1,4-dioate; (N-methoxy-N-methylcarbamoyl)methyl methyl (2E)but-2-ene-1,4-dioate; bis-(2-methoxyethylamino) carbamoyl]methyl methyl(2E)but-2-ene-1,4-dioate; [N-(methoxycarbonyl)carbamoyl]methyl methyl(2E)but-2ene-1,4-dioate; 4-{2-[(2E)-3-(methoxycarbonyl)prop-2-enoyloxy]acetylamino}butanoic acid, sodium salt; methyl 2-oxo-2-piperazinylethyl(2E)but-2-ene-1,4-dioate; methyl 2-oxo-2-(2-oxo(1,3-oxazolidin-3-yl)ethyl(2E)but-2ene-1,4-dioate; {N-[2-(dimethylamino)ethyl]carbamoyl}methyl methyl(2E)but-2ene-1,4 dioate; methyl 2-(4-methylpiperazinyl)-2-oxoethyl(2E)but-2-ene-1,4-dioate; methyl {N-[(propylamino)carbonyl]carbamoyl}methyl(2E)but-2ene-1,4-dioate; 2-(4-acetylpiperazinyl)-2-oxoethyl methyl(2E)but-2ene-1,4-dioate; {N,N-bis[2-(methylethoxy)ethyl]carbamoyl}methyl methyl(2E)but-2-ene-1,4-dioate; methyl 2-(4-benzylpiperazinyl)-2-oxoethyl(2E)but-2-ene-1,4-dioate; [N,N-bis(2-ethoxyethyl)carbamoyl]methyl methyl(2E)but-2-ene-1,4-dioate; 2-((2S)-2-[(tert-butyl)oxycarbonyl] pyrrolidinyl)-2-oxoethyl methyl(2E)but-2ene-1,4-dioate; 1-{2-{(2E)-3-(methoxycarbonyl)prop-2-enoyloxy]acetyl} (2S)pyrrolidine-2-carboxylic acid; (N-{[tert-butyl)oxycarbonyl]methyl}-N-methylcarbamoyl)methyl methyl(2E)but-2ene-1,4-dioate; {N-(ethoxycarbonyl)methyl]-N-methylcarbamoyl}methyl methyl(2E)but-2-ene-1,4-dioate; methyl 1-methyl-2-morpholin-4-yl-2-oxoethyl(2E)but-2-ene-1,4-dioate; [N,N-bis(2-methoxyethyl)carbamoyl]ethyl methyl(2E)but-2-en-1,4-dioate; (N,N-dimethylcarbamoyl) ethyl methyl(2E)but-2-ene-1,4-dioate; 2-{2-[(2E)-3-(methoxy carbonyl)prop-2-enoyloxyl]-N-methylacetylamino}acetic acid; (N-([(tert-butyl) oxycarbonyl]methyl)carbamoyl)methyl methyl(2E)but-2-ene-1,4-dioate; (2E)but-methyl-N-{[(methylethyl) oxycarbonyl]methyl}carbamoyl)methyl(2E)but-2-ene-1,4-dioate; {N-[(ethoxycarbonyl)methyl]-N-benzylcarbamoyl}methyl methyl(2E)but-2-ene-1,4-dioate; {N-[(ethoxycarbonyl)methyl]-N-benzylcarbamoyl}ethyl methyl(2E)but-2-ene-1,4-dioate; {N-[(ethoxycarbonyl) methyl]-N-methylcarbamoyl}ethyl methyl(2E)but-2-ene-1,4-dioate; (1S)-1-methyl-2-morpholin-4-yl-2-oxo ethyl methyl(2E)but-2-ene-1,4-dioate; (1S)-1-[N,N-bis(2-methoxyethyl)carbamoyl]ethyl methyl(2E)but-2-ene-1,4-dioate; (1R)-1-(N,N-diethylcarbamoyl)ethyl methyl(2E)but-2-ene-1,4-dioate; and a pharmaceutically acceptable salt of any of the foregoing.

Useful examples of a compound of Formula (I) also include: (N,N-diethylcarbamoyl)methyl methyl(2E)but-2-ene-1,4-dioate; methyl[N-benzylcarbamoyl]methyl(2E)but-2-ene-1,4-dioate; methyl 2-morpholin-4-yl-2-oxoethyl(2E) but-2-ene-1,4-dioate; (N-butylcarbamoyl)methyl methyl (2E)but-2-ene-1,4-dioate; [N-(2-methoxyethyl)carbamoyl] methyl methyl(2E)but-2-ene-1,4-dioate; 2-(2-[(2E)-3-(methoxycarbonyl)prop-2-enoyloxy)acetylamino)acetic acid; {2-[(2E)-3-(methoxycarbonyl)prop-2-enoyloxy] acetylamino}butanoic acid; methyl(N-(1,3,4-thiadiazol-2-yl)carbamoyl)methyl(2E)but-2ene-1,4-dioate; (N,N-dimethylcarbamoyl)methyl methyl(2E)but-2-ene-1,4-dioate; (N-methoxy-N-methylcarbamoyl)methyl methyl(2E)but-2-ene-1,4-dioate; bis-(2-methoxyethylamino)carbamoyl] methyl methyl(2E)but-2-ene-1,4-dioate; [N-(methoxycarbonyl)carbamoyl]methyl methyl(2E)but-2-ene-1,4-dioate; methyl 2-oxo-2-piperazinylethyl(2E)but-2-ene-1,4-dioate; methyl 2-oxo-2-(2-oxo(1,3-oxazolidin-3-yl)ethyl(2E)but-2ene-1,4-dioate; {N-[2-(dimethylamino)ethyl] carbamoyl}methyl methyl(2E)but-2-ene-1,4-dioate; (N-

[(methoxycarbonyl)ethyl]carbamoyl)methyl methyl(2E)but-2-ene-1,4-dioate; 2-{2-[(2E)-3-(methoxycarbonyl)prop-2-enoyloxy]acetylamino}propanoic acid; and a pharmaceutically acceptable salt of any of the foregoing.

Compounds that can be metabolized into MMF in vivo also include compounds of Formula II:

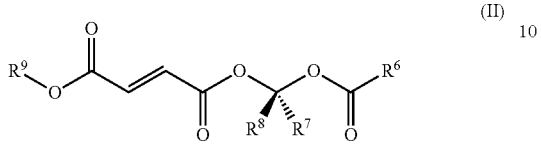

(II)

or a pharmaceutically acceptable salt thereof, wherein
$R^6$ is chosen from $C_{1-6}$ alkyl, substituted $C_{1-6}$ alkyl, $C_{1-6}$ heteroalkyl, substituted $C_{1-6}$ heteroalkyl, $C_{3-8}$ cycloalkyl, substituted $C_{3-8}$ cycloalkyl, $C_{6-8}$ aryl, substituted $C_{6-8}$ aryl, and —$OR^{10}$ wherein $R^{10}$ is chosen from $C_{1-6}$ alkyl, substituted $C_{1-6}$ alkyl, $C_{3-10}$ cycloalkyl, substituted $C_{3-10}$ cycloalkyl, $C_{6-10}$ aryl, and substituted $C_{6-10}$ aryl;
$R^7$ and $R^8$ are independently chosen from hydrogen, $C_{1-6}$ alkyl, and substituted $C_{1-6}$ alkyl; and
$R^9$ is chosen from $C_{1-6}$ alkyl and substituted $C_{1-6}$ alkyl;
wherein each substituent group is independently chosen from halogen, —OH, —CN, —$CF_3$, =O, —$NO_2$, benzyl, —C(O)$NR^{11}_2$, —$R^{11}$, —$OR^{11}$, —C(O)$R^{11}$, —COO$R^{11}$, and —$NR^{11}_2$ wherein each $R^{11}$ is independently chosen from hydrogen and $C_{1-4}$ alkyl.

Useful examples of a compound of Formula (II) include: ethoxycarbonyloxyethyl methyl(2E)but-2-ene-1,4-dioate; methyl(methylethoxycarbonyloxy)ethyl(2E)but-2-ene-1,4-dioate; (cyclohexyloxycarbonyloxy)ethyl methyl(2E)but-2-ene-1,4-dioate; and a pharmaceutically acceptable salt of any of the foregoing.

Additional useful examples of a compound of Formula (II) include: methyl(2-methylpropanoyloxy)ethyl(2E)but-2-ene-1,4-dioate; methyl phenylcarbonyloxyethyl(2E)but-2-ene-1,4-dioate; cyclohexylcarbonyloxybutyl methyl(2E)but-2-ene-1,4-dioate; [(2E)-3-(methoxycarbonyl)prop-2-enoyloxy]ethyl methyl(2E)but-2-ene-1,4-dioate; methyl 2-methyl-1-phenylcarbonyloxypropyl(2E)but-2-ene-1,4-dioate; and a pharmaceutically acceptable salt of any of the foregoing.

Useful examples of a compound of Formula (II) also include: ethoxycarbonyloxyethyl methyl(2E)but-2-ene-1,4-dioate; methyl(methylethoxycarbonyloxy)ethyl(2E)but-2-ene-1,4-dioate; methyl(2-methylpropanoyloxy)ethyl(2E)but-2-ene-1,4-dioate; methyl phenylcarbonyloxyethyl(2E)but-2-ene-1,4-dioate; cyclohexylcarbonyloxybutyl methyl (2E)but-2-ene-1,4-dioate; [(2E)-3-(methoxycarbonyl)prop-2-enoyloxy]ethyl methyl(2E)but-2-ene-1,4-dioate; (cyclohexyloxycarbonyloxy)ethyl methyl(2E)but-2-ene-1,4-dioate; methyl 2-methyl-1-phenylcarbonyloxypropyl(2E)but-2-ene-1,4-dioate; 3-({[(2E)-3-(methoxycarbonyl)prop-2-enoyloxy]methyl}oxycarbonyl)(3S)-3-aminopropanoic acid, 2,2,2-trifluoroacetic acid; 3-({[(2E)-3-(methoxycarbonyl)prop-2-enoyloxy]methyl}oxycarbonyl)(2S)-2-aminopropanoic acid, 2,22-trifluoroacetic acid; 3-({[(2E)-3-(methoxycarbonyl)prop-2-enoyloxy]methyl}oxycarbonyl)(3S)-3-(2-aminoacetylamino)propanoic acid, 2,2,2-trifluoroacetic acid; 3-({[(2E)-3-(methoxycarbonyl)prop-2-enoyloxy]methyl}oxycarbonyl)(2S)-2-aminopropanoic acid, 2,2,2-trifluoroacetic acid; 3-{[(2E)-3-(methoxycarbonyl)prop-2enoyloxy]ethoxycarbonyloxy}(2S)-2-aminopropanoic acid, chloride; and a pharmaceutically acceptable salt of any of the foregoing.

Compounds that can be metabolized into MMF in vivo also include compounds of Formula (III):

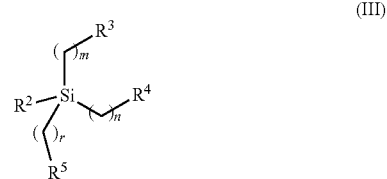

(III)

or a pharmaceutically acceptable salt thereof, wherein:
$R^2$ is $C_1$-$C_{10}$ alkyl, $C_5$-$C_{15}$ aryl, hydroxyl, —O—$C_1$-$C_{10}$ alkyl, or —O—$C_5$-$C_{15}$ aryl; each of $R^3$, $R^4$, and $R^5$, independently, is $C_1$-$C_{10}$ alkyl, $C_5$-$C_{15}$ aryl, hydroxyl, —O—$C_1$-$C_{10}$ alkyl, —O—$C_5$-$C_{15}$ aryl, or

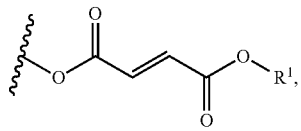

wherein $R^1$ is $C_1$-$C_{24}$ alkyl or $C_5$-$C_{50}$ aryl; each of which can be optionally substituted; and
each of m, n, and r, independently, is 0-4;
provided that at least one of $R^3$, $R^4$, and $R^5$ is

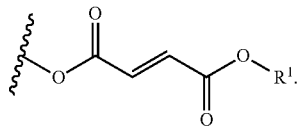

Useful examples of a compound of formula (III) include (dimethylsilanediyl)dimethyl difumarate; methyl ((trimethoxysilyl)methyl) fumarate; methyl ((trihydroxysilyl)methyl) fumarate; trimethyl (methylsilanetriyl) trifumarate; and a pharmaceutically acceptable salt of any of the foregoing.

Compounds that can be metabolized into MMF in vivo also include compounds of Formula (IV):

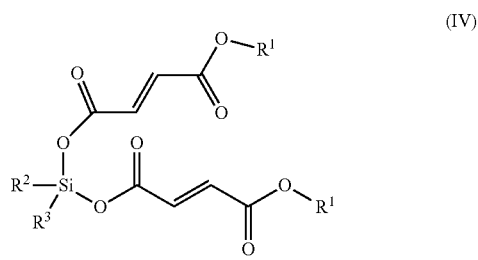

(IV)

or a pharmaceutically acceptable salt thereof, wherein:
each of, independently, $R^2$ and $R^3$, is $C_1$-$C_{10}$ alkyl or $C_5$-$C_{15}$ aryl.
$R^2$ and $R^3$ can be the same or different, can be optionally substituted, and independently can be selected from the group consisting of $C_1$-$C_{10}$ alkyl or $C_5$-$C_{15}$ aryl.

Compound that can be metabolized into MMF in vivo also include compounds of Formula (V):

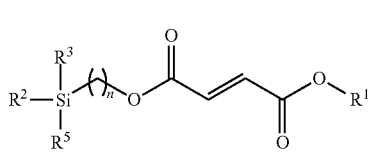

or a pharmaceutically acceptable salt thereof, wherein:
$R^1$ is $C_1$-$C_{24}$ alkyl or $C_5$-$C_{50}$ aryl;
each of $R^2$, $R^3$, and $R^5$, independently, is hydroxyl $C_1$-$C_{10}$ alkyl, $C_5$-$C_{15}$ aryl, —O—$C_1$-$C_{10}$ alkyl, or —O—$C_5$-$C_{15}$ aryl; and
n is 1 or 2.

Additional compounds that can be metabolized into MMF in vivo include compounds of Formula (VI):

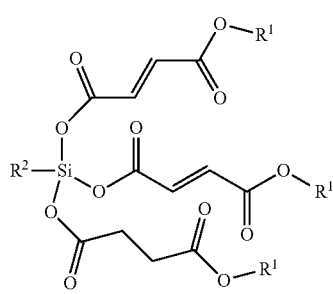

or a pharmaceutically acceptable salt thereof, wherein:
$R^1$ is $C_1$-$C_{24}$ alkyl or $C_5$-$C_{50}$ aryl; and
$R^2$ is $C_1$-$C_{10}$ alkyl.

As used herein, the term "fumarate agent" refers to MMF, a compound that can be metabolized into MMF in vivo (e.g., DMF), or a pharmaceutically acceptable salt thereof or combinations thereof, or deuterated analogues thereof. In some embodiments, the fumarate agent can include more than one compound, for example, a combination of MMF and DMF. In some embodiments, the fumarate agent is a single compound, e.g., DMF.

Useful examples of deuterated analogs include compounds of formula (VII): a compound of formula (I)

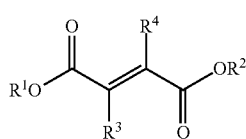

or a pharmaceutically acceptable salt thereof, wherein
each of $R^1$ and $R^2$, independently, is hydrogen, deuterium, deuterated methyl, deuterated ethyl, $C_{1-6}$ aliphatic, phenyl, 3-7 membered saturated or partially unsaturated monocyclic carbocyclic ring, 3-7 membered saturated or partially unsaturated monocyclic heterocyclic ring having 1-3 heteroatoms independently selected from nitrogen, oxygen, and sulfur, or a 5-6 membered heteroaryl ring having 1-3 heteroatoms independently selected from nitrogen, oxygen, and sulfur, and each of $R^3$ and $R^4$, independently, is hydrogen or deuterium, provided that the compound of formula (VII) contains at least one deuterium atom and that $R^1$ and $R^2$ are not hydrogen at the same time.

Useful examples of compounds of formula (VII) include ($^2H_6$)dimethyl fumaric acid ester, ($^2H_3$)methyl fumaric acid ester, ($^2H_3$)dimethyl fumaric acid ester, dimethyl fumaric(2,3-$^2H_2$) acid ester, methyl fumaric(2,3-$^2H_2$) acid ester, ethyl fumaric(2,3-$^2H_2$) acid ester, ($^2H_3$)methyl fumaric(2,3-$^2H_2$) acid ester, ($^2H_6$)dimethyl fumaric(2,3-$^2H_2$) acid ester, methyl (2-morpholino-2-oxoethyl) fumaric(2,3-$^2H_2$) acid ester, methyl (4-morpholino-1-butyl) fumaric(2,3-$^2H_2$) acid ester, 2-(benzoyloxy)ethyl methyl fumaric(2,3-$^2H_2$) acid ester, 2-(benzoyloxy)ethyl ($^2H_3$)methyl fumaric acid ester, (S)-2-((2-amino-3-phenylpropanoyl)oxy)ethyl methyl fumaric(2,3-$^2H_2$) acid ester, or (S)-2-((2-amino-3-phenylpropanoyl)oxy)ethyl ($^2H_3$)methyl fumaric acid ester.

4.3 Method 1. Treating a Subject Who May Receive a Vaccine

4.3.1 Method 1a

In some embodiments, the invention provides a method of treating or preventing a disease or disorder (e.g., MS) in a subject in need thereof, comprising
(a) administering to the subject a first dose of a pharmaceutical composition for a first dosing period, wherein the pharmaceutical composition comprises a fumarate agent selected from the group consisting of monomethyl fumarate, a compound that metabolizes into monomethyl fumarate in vivo, a deuterated analog thereof, a pharmaceutically acceptable salt thereof, and a combination thereof;
(b) administering a vaccine to the subject; and
(c) administering to the subject a second dose of the pharmaceutical composition for a second dosing period, wherein the second dosing period is after the first dosing period. In some embodiments, the disease or disorder is MS. In some embodiments, the second dose is about 0 In about 480 mg fumarate agent.

4.32 Method 1b

In some embodiments, the invention provides a method of treating or preventing a disease or disorder (e.g., MS) in a subject in need thereof, comprising
(a) administering to the subject a first dose of a pharmaceutical composition for a first dosing period, wherein the pharmaceutical composition comprises a fumarate agent selected from the group consisting of monomethyl fumarate, a compound that metabolizes into monomethyl fumarate in vivo, a deuterated analog thereof, a pharmaceutically acceptable salt thereof, and a combination thereof, and wherein the subject receives a vaccine;
(b) determining an immune response of the subject to the vaccine before the end of the first dosing period; and
(c) adjusting the first dose to a second dose of the pharmaceutical composition, which includes stopping administration of the pharmaceutical composition (i.e., the second dose can be about 0 to about 480 mg fumarate agent), based on the immune response determined in step (b).

4.3.3 Method 1c

In some embodiments, the invention provides a method of treating or preventing a disease or disorder (e.g., MS) in a subject in need thereof, comprising (a) administering to the subject a first dose of a pharmaceutical composition for a first dosing period, wherein the pharmaceutical composition comprises a fumarate agent selected from the group consisting of monomethyl fumarate, a compound that metabolizes into monomethyl fumarate in vivo, a deuterated analog thereof, a pharmaceutically acceptable salt thereof, and a combination thereof, and wherein the subject receives a vaccine;
(b) determining an immune response of the subject to the vaccine before the end of the first dosing period; and
(c) administering to the subject a second dose of the pharmaceutical composition for a second dosing period. In some embodiments, the second dose is equal to or less than the first dose.

4.3.4 Method 1d

In some embodiments, the invention provides a method of treating or preventing multiple sclerosis in a subject in need thereof, comprising
(a) determining a subject's baseline lymphocyte count prior to treatment;
(b) administering to the subject a first dose of a pharmaceutical composition for a first dosing period, wherein the pharmaceutical composition comprises a fumarate agent selected from the group consisting of monomethyl fumarate, a compound that metabolizes into monomethyl fumarate in vivo, a deuterated analog thereof, a pharmaceutically acceptable salt thereof, and a combination thereof;
(c) determining a subject's total lymphocyte count after the first dosing period; and
(d) if the lymphocyte count after the first dosing period is 90% of the baseline lymphocyte count or lower, do not administer tetanus diphtheria toxoids vaccine, keyhole limpet hemocyanin vaccine, pneumovax-23 vaccine, or any combinations thereof.

4.3.5 Method 1e

In some embodiments, the invention provides a method of treating multiple sclerosis in a human subject in need thereof comprising
(a) administering a therapeutically effective amount of dimethyl fumarate to the subject; and
(b) administering a vaccine to the subject.

In one embodiment, the therapeutically effective amount of dimethyl fumarate is a maintenance dose that is repeatedly administered over at least a period of time, and said step (b) of administering said vaccine is during said period of time.

The period of time can be, for example, for at least one, two, three, four, five, six, or seven days, or for at least one, two, three, or four weeks, or for at least one, two, three, four, five, six, seven, eight, nine, ten, eleven, twelve months, or longer. In one embodiment, the period of time is 1 week. In another embodiment, the period of time is 6 months. In a specific embodiment, the maintenance dose is administered after a time period during which the administered dosage is lower than the maintenance dose. For example, administration of a maintenance dose of 240 mg dimethyl fumarate administered orally twice daily can be immediately preceded by a time period of uptitration consisting of orally administered 120 mg dimethyl fumarate twice daily for 7 days. As another example, administration of a maintenance dose of 240 mg dimethyl fumarate administered orally twice daily can be immediately preceded by a time period of uptitration consisting of orally administering a starting dose of 120 mg dimethyl fumarate daily for 2 weeks, followed by 120 mg dimethyl fumarate twice daily for 2 weeks, followed by 360 mg dimethyl fumarate daily for 2 weeks; wherein the 360 mg dimethyl fumarat daily is 240 mg dimethyl fumarate in the morning and 120 mg dimethyl fumarate in the evening.

In one embodiment, the maintenance dose is orally administered 480 mg dimethyl fumarate daily. In a specific embodiment, the maintenance dose is orally administered 240 mg dimethyl fumarate twice daily.

In one embodiment, the immune response to said vaccine is decreased in said subject relative to the immune response in the absence of said step (a) of administering a therapeutically effective amount of dimethyl fumarate.

In one embodiment, the multiple sclerosis is a relapsing form of multiple sclerosis.

In one embodiment, the multiple sclerosis is relapsing-remitting multiple sclerosis

4.3.6 Diseases and Disorders

Suitable diseases and disorders that can be treated by the fumarate agent are known in the art, which include any diseases or disorders where administering DMF is helpful.

In some embodiments, the disease or disorder where administering DMF is helpful is
(1) an autoimmune disease selected from the group consisting of polyarthritis, rheumatoid arthritis, multiple sclerosis, graft-versus-host reactions, juvenile-onset diabetes, Hashimoto's thyroiditis, Grave's disease, systemic Lupus crythematodes (SLE), Sjogren's syndrome, pernicious anaemia and chronic active (=lupoid) hepatitis, psoriasis, psoriatic arthritis, neurodermatitis and enteritis regionalis Crohn;
(2) a mitochondrial disease selected from the group consisting of Parkinson syndrome, Alzheimer's disease, Chorea Huntington disease, retinopathia pigmentosa or forms of mitochondrial encephalomyopathy;
(3) a NF-kappaB mediated diseases selected from the group consisting of progressive systemic sclerodermia, osteochondritis syphilitica (Wegener's disease), cutis marmorata (livedo reticularis), Behcet disease, panarteriitis, colitis ulcerosa, vasculitis, osteoarthritis, gout, artenosclerosis, Reiter's disease, pulmonary granulomatosis, types of encephalitis, endotoxic shock (septic-toxic shock), sepsis, pneumonia, encephalomyclitis, anorexia nervosa, hepatitis (acute hepatitis, chronic hepatitis, toxic hepatitis, alcohol-induced hepatitis, viral hepatitis, jaundice, liver insufficiency and cytomegaloviral hepatitis), Rennert T-lymphomatosis, mesangial nephritis, post-angioplastic restenosis, reperfusion syndrome, cytomegaloviral retinopathy, adenoviral diseases such as adenoviral colds, adenoviral pharyngoconjunctival fever and adenoviral ophthalmia, AIDS, Guillain-Barré syndrome, post-herpetic or post-zoster neuralgia, inflammatory demyelinising polyneuropathy, mononeuropathia multiplex, mucoviscidosis, Bechterew's disease, Barett oesophagus, EBV (Epstein-Barr virus) infection, cardiac remodeling, interstitial cystitis, diabetes mellitus type II, human tumour radiosensitisation, multi-resistance of malignant cells to chemotherapeutic agents (multidrug resistance in chemotherapy), granuloma annulare and cancers such as mamma carcinoma, colon carcinoma, melanoma, primary liver cell carcinoma, adenocarcinoma, kaposi's sarcoma, prostate carcinoma, leukaemia such as acute myeloid leukaemia, multiple myeloma (plasmocytoma), Burkitt lymphoma and Castleman tumour;

(4) a cardiovascular disease selected from the group consisting of cardiac insufficiency, myocardial infarct, angina pectoris and combinations thereof;

(5) a respiratory disease selected from the group consisting of asthma, chronic obstructive pulmonary diseases, PDGF induced thymidine uptake of bronchial smooth muscle cells, bronchial smooth muscle cell proliferation, and combinations thereof, (6) a neurodegeneration or neuroinflammation selected from the group consisting of Adrenal Leukodystrophy (ALD), Alcoholism, Alexander's disease, Alper's disease, Alzheimer's disease, Amyotrophic lateral sclerosis (Lou Gehrig's Disease), Ataxia telangiectasia, Batten disease (also known as Spielmeyer-Vogt-Sjögren-Batten disease), Bovine spongiform encephalopathy (BSE), Canavan disease, Cerbral palsy, Cockayne syndrome, Corticobasal degeneration, Creutzfeldt-Jakob disease, Familial Fatal Insomnia, Frontotemporal lobar degeneration, Huntington's disease, HIV-associated dementia, Kennedy's disease, Krabbe's disease, Lewy body dementia, Neuroborreliosis, Machado-Joseph disease (Spinocerebellar ataxia type 3), Multiple System Atrophy, Multiple sclerosis, Narcolepsy, Niemann Pick disease, Parkinson's disease, Pelizaeus-Merzbacher Disease, Pick's disease, Primary lateral sclerosis, Prion diseases, Progressive Supranuclear Palsy, Refsum's disease, Sandhoff disease, Schilder's disease, Subacute combined degeneration of spinal cord secondary to Pernicious Anaemia, Spielmeyer-Vogt-Sjögren-Batten disease (also known as Batten disease), Spinocerebellar ataxia, Spinal muscular atrophy, Steele-Richardson-Olszewski disease, Tabes dorsalis, Toxic encephalopathy, LHON (Leber's Hereditary optic neuropathy), MELAS (Mitochondrial Encephalomyopathy; Lactic Acidosis; Stroke), MERRF (Myoclonic Epilepsy; Ragged Red Fibers), PEO (Progressive External Opthalmoplegia), Leigh's Syndrome, MNGIE (Myopathy and external ophthalmoplegia; Neuropathy; Gastro-Intestinal; Encephalopathy), Kearns-Sayre Syndrome (KSS), NARP, Hereditary Spastic Paraparesis, Mitochondrial myopathy, and Friedreich Ataxia; or (7) a demyelinating neurological disorder selected from the group consisting of optic neuritis, acute inflammatory demyelinating polyneuropathy (AIDP), chronic inflammatory demyelinating polyneuropathy (CIDP), acute transverse myelitis, progressive multifocal leucoencephalopathy (PML), acute disseminated encephalomyelitis (ADEM) or other hereditary disorders (e.g., leukodystrophies, Leber's optic atrophy, and Charcot-Marie-Tooth disease).

In some embodiments, the disease or disorder where administering DMF is helpful is a neutrophil mediated disease or disorder (e.g., an allergic disease or disorder, an inflammatory disease or disorder, an autoimmune disease or disorder, or a tumor).

Non-limiting examples of autoimmune diseases or disorders include autoimmune Addison's disease, autoimmune hemolytic anemia, autoimmune hepatitis, autoimmune inner ear disease, autoimmune lymphoproliferative syndrome (ALPS), autoimmune thrombocytopenic purpura (ATP), or autoimmune skin blistering diseases (AIBD).

Non-limiting examples of autoimmune skin blistering diseases include epidermolysis bullosa acquistita (EBA), pemphigoid disease (e.g., bullous pemphigoid, mucous membrane pemphigoid, or pemphigoid gestationis), IgA-mediated bullous dermatoses (e.g., Dermatitis Herpetiformis or Linear IgA Bullous Dermatosis), and pemphigus disease (e.g., IgA Pemphigus).

Non-limiting neutrophil mediated diseases or disorders also include an inflammatory skin or subcuteneous disease selected from the group consisting of Pyoderma Gangrenosum, Erosive Pustular Dermatosis of the Scalp, Sweet's Syndrome, Bowel-associated Dermatosis-arthritis Syndrome, Pustular Psoriasis, Acute Generalized Exanthematous Pustulosis, Keratoderma Blenorrhagicum, Sneddon-Wilkinson Disease, Amicrobial Pustulosis of the Folds, Infantile Acropustulosis, Transient Neonatal Pustulosis, Neutrophilic Eccrine Hidradenitis, Rheumatoid Neutrophilic Dermatitis, Neutrophilic Urticaria, Still's Disease. Erythema Marginatum, Unclassified Periodic Fever Syndromes/Autoinflammatory Syndromes, Bullous Systemic Lupus Erythematosus, and Neutrophilic Dermatosis of the Dorsal Hands (Pustular Vasculitis);

Non-limiting neutrophil mediated diseases or disorders also include:

a) an allergic condition selected from the group consisting of anaphylaxis, allergic rhinitis and allergic asthma;

b) neutrophil mediated respiratory disease selected from the group consisting of lung cancer, severe asphyxic episodes of asthma, acute lung injury, and Acute Respiratory Distress Syndrome;

c) an acute tissue injury selected from the group consisting of acute kidney injury, ischemia reperfusion injury, sepsis, and septicemia with multiorgan failure;

d) an inflammatory bowel disease selected from the group consisting of ulcerative colitis, Crohn's disease, and indeterminate colitis; and e) sickle cell crisis or acute chest syndrome.

In some embodiments, the disease or disorder where administering DMF is helpful is a disease or disorder that is associated with aberrant PI3K/AKT signaling, including cancer, chronic inflammation and allergy, neurodegenerative disease, cardiovascular disease and metabolic diseases. Non-limiting examples of disease or disorders that are associated with aberrant PI3K/AKT signaling include all forms of cancer, precancerous lesions, cardiovascular disease, rheumatologic disease, pulmonary disease, dermatologic disease, gynecological diseases, vascular disease, neurologic disease, and infectious disease including bacterial, viral, retroviral, and parasitic diseases. In some embodiments, the disease or disorder to be treated is cancer. Non-limiting examples of cancer include breast cancer, lung cancer, ovarian cancer, uterine cancer, brain cancer, sarcoma, melanoma, leukemia, lymphoma, colorectal cancer, prostate cancer, and liver cancer. In some embodiments, the disease or disorder to be treated is rheumatologic disease, e.g., rheumatoid arthritis or osteoarthritis. In some embodiments, the disease or disorder to be treated is pulmonary disease, e.g., allergic rhinitis, chronic obstructive pulmonary disease (COPD).

In some embodiments, the disease or disorder where administering DMF is helpful is a disease or disorder that is associated with aberrant p38 MAPK signaling. Non-limiting examples of such diseases include COPD (including chronic bronchitis and emphysema), asthma, pediatric asthma, cystic fibrosis, sarcoidosis, idiopathic pulmonary fibrosis, allergic rhinitis, rhinitis, sinusitis, allergic conjunctivitis, conjunctivitis, allergic dermatitis, contact dermatitis, psoriasis, ulcerative colitis, inflamed joints secondary to rheumatoid arthritis or osteoarthritis, rheumatoid arthritis, pancreatitis, cachexia, inhibition of the growth and metastasis of tumours including non-small cell lung carcinoma, breast carcinoma, gastric carcinoma, colorectal carcinomas and malignant melanoma.

In some embodiments, the disease or disorder is a neurological disease or disorder. In some embodiments, the neurological disease or disorder is an autoimmune disease. In some embodiments, the neurological disease or disorder is a demyelinating disease or disorder.

In some embodiments, the neurological disease or disorder is selected from the group consisting of multiple sclerosis (MS), Huntington's disease, Alzheimer's disease, Parkinson's disease, optic neuritis, Devic disease, transverse myelitis, acute disseminated encephalomyelitis, adrenoleukodystrophy and adrenomyeloneuropathy, acute inflammatory demyelinating polyneuropathy (AIDP), chronic inflammatory demyelinating polyneuropathy (CIDP), acute transverse myelitis, progressive multifocal leucoencephalopathy (PML), acute disseminated encephalomyclitis (ADEM) and other hereditary disorders, such as leukodystrophies, Leber's optic atrophy, and Charcot-Marie-Tooth disease.

In some embodiments, the neurological disease or disorder is multiple sclerosis. In some embodiments, the MS is relapsing remitting MS, secondary progressive MS, primary progressive MS, progressive relapsing MS, or clinically isolated syndrome (CIS). In some embodiments, the neurological disease or disorder is a relapsing form of MS.

4.3.7 Vaccination Schedule

Various vaccination schedules are suitable for the methods described herein. In some embodiments, the subject receives the vaccine during the first dosing period. For example, the subject can receive the vaccine from one week to 24 weeks (e.g., 1 week, 2 weeks, 4 weeks, 8 weeks, 12 weeks, 16 weeks, 20 weeks, 24 weeks, or any ranges thereof) before the start of the first dosing period. In some embodiments, the subject receives the vaccine more than 24 weeks (e.g., more than 48 weeks, more than 96 weeks, or more than 5 years) before the start of the first dosing period. In some embodiments, the subject receives the vaccine during the first dosing period, for example, from 1 week to 48 weeks (e.g., 1 week, 2 weeks, 4 weeks, 8 weeks, 12 weeks, 16 weeks, 20 weeks, 24 weeks, 36 weeks, 48 weeks, or any ranges thereof) after the start of the first dosing period. In some embodiments, the subject receives the vaccine from 1 week to 48 weeks (e.g., 1 week, 2 weeks, 4 weeks, 8 weeks, 12 weeks, 16 weeks, 20 weeks, 24 weeks, 36 weeks, 48 weeks, or any ranges thereof) before the end of the first dosing period. In some embodiments, the subject receives at least one vaccine (e.g., 2 vaccines, 3 vaccines, 4 vaccines, or more than 4 vaccines) during the first dosing period. In some embodiments, each vaccine contains either a single antigen or multiple antigens.

In some embodiments, the first dosing period lasts from 1 month to 2 years (e.g., 1 month, 3 months, 6 months, 1 year, 2 year, or any ranges thereof). In some embodiments, the first dosing period is more than 2 years (e.g., more than 3 years, or more than 5 years). In some embodiments, the first dosing period lasts until the vaccine is administered to the subject.

In some embodiments, the second dosing period lasts from 1 week to 2 years (e.g., 1 week, 1 month, 3 months, 6 months, 1 year, 2 year, or any ranges thereof). In some embodiments, the second dosing period is more than 2 years (e.g., more than 3 years, more than 5 years, or for life). In some embodiments, the second dosing period lasts less than 1 week (e.g., 1, 2, 3, 4, 5, or 6 days). In some embodiments, the second dosing period is initiated within a week of (e.g., 1 day, 2 days, 3 days, 4 days, 5 days, 6 days, or 7 days after) the end of the first dosing period. In some embodiments, the second dosing period is initiated 1 week to 48 weeks (e.g., 1 week, 2 weeks, 4 weeks, 8 weeks, 12 weeks, 16 weeks, 20 weeks, 24 weeks, 36 weeks, 48 weeks, or any ranges thereof) after the end of the first dosing period. In some embodiments, the second dosing period is initiated on the same day on which the first dosing period ends. In other embodiments, the second dosing period is initiated on the same day as the subject receives a vaccine.

4.3.8 First and Second Doses

Various amounts of the fumarate agent can be used for the first and second doses in the methods described herein. In some embodiments, the first or second dose of the pharmaceutical composition contains a therapeutically effective amount of the fumarate agent. In some embodiments, the fumarate agent comprises MMF, DMF, or a combination thereof. In some embodiments, the fumarate agent comprises DMF. In some embodiments, the only active ingredient in the pharmaceutical composition is DMF. In a preferred embodiment, the pharmaceutical composition is Tecfidera® which is a controlled-release microtablet formulation containing 240 mg of DMF per capsule and the first or second dose of the pharmaceutical composition is effected by administering a Tecfidera® capsule to the subject twice daily or three times daily. In one embodiment, the first or second dose of the pharmaceutical composition is effected by administering a Tecfidera® capsule to the subject twice daily for a total daily dose of 480 mg.

In some embodiments, the second dose is no greater than the first dose. In some embodiments, the second dose is the same as the first dose. In some embodiments, the second dose is about 5% to about 95% (e.g., about 10%, about 20%, about 30%, about 40%, about 50%, about 60V, about 70%, about 80%, about 90%, or any ranges thereof) of the first dose. For example, the first dose can be a daily amount of about 480 mg of DMF, e.g., effected by a BID dosing, and the second dose can be 50% of the first dose, which is a daily amount of about 240 mg of DMF, which can also be effected by a BID dosing. In some embodiments, the second dose is less than 50% of the first dose. In some embodiments, the second dose is a daily amount of about 0 to about 480 mg fumarate agent. In some embodiments, the second dose is a daily amount of about 120 mg, about 240 mg, about 360 mg, or about 480 mg fumarate agent administered to the subject in 1, 2, or 3 (e.g., equal) doses. In some embodiments, the second dose is 0 mg fumarate agent.

In some embodiments, the subject is administered the same amount of fumarate agent as in the first dosing period after the second dosing period.

In some embodiments, the methods described herein further comprises administering a titration dose of the pharmaceutical composition prior to the first and/or second dosing period. In some embodiments, the titration dose is administered to the subject for at least 7 days prior to beginning the first or second dosing period. In some embodiments, the fumarate agent is DMF and the titration dose is a daily dose of about 240 mg DMF administered BID for 7 consecutive days. In some embodiments, the fumarate agent is DMF and the titration dose is a daily dose of 360 mg DMF administered three times a day for 7 consecutive days.

The pharmaceutical composition can be in different forms. Non-limiting examples include pills, tablets, microtablets, pellets, powders, granules, micropellets, capsules (e.g., containing microtablets), liquid formulations for oral administration, and the form of dietary supplements. Methods for preparing pharmaceutical compositions in these forms are known in the art. Suitable pharmaceutically acceptable excipients for preparing the pharmaceutical compositions are also known in the art, for example, binders, fillers, disintegrants, glidants, lubricants, diluents, plasticizers, etc. as described in Remington's Pharmaceutical Science, 18$^{th}$ Edition, 1990, Mack Publishing Company, Easton, Pa. ("Remington's").

In some embodiments, the pharmaceutical composition is in the form of a capsule (such as a soft or hard gelatine capsule) containing DMF in the form of microtablets or micropellets (e.g., enteric-coated microtablets or micropellets). Suitable microtablets or micropellets are, without limitation, those having a mean diameter of 5,000 microns or less (e.g., 4,000 microns or less, 3,000 microns or less, 2,000 microns or less, 1,000 microns or less, or 500 microns or less) exclusive of any optional coating applied to the microtablets or micropellets. In some embodiments, the pharmaceutical composition is in the form of a capsule containing a pharmaceutical preparation consisting essentially of 60-240 mg (e.g., 120 mg, or 240 mg) of DMF in the form of enteric-coated microtablets. In some embodiments, the mean diameter of such microtablets is 1,000-5,000 microns, e.g., 1,000-3,000 microns or 2,000 microns. Methods for preparing microtablets or micropellets (e.g., enteric-coated microtablets or micropellets) comprising DMF are known in the art, for example, as described in U.S. Pat. No. 6,509,376 and incorporated by reference in its entirety herein.

The pharmaceutical composition suitable for the methods described herein include without limitation those formulated as an enterically coated immediate release dosage form, or a controlled release dosage form (e.g., a delayed release dosage form, a sustained release dosage form, a pulsatile release dosage form). In some embodiments, the controlled release dosage form is a gastric retentive dosage form. In some embodiments, the pharmaceutical composition is formulated as an enterically coated immediate release dosage form. In some embodiments, the pharmaceutical composition is formulated as a delayed release dosage form. The fumarate agent (e.g., DMF, MMF, or a combination thereof) can be administered in the form of a sustained or controlled release pharmaceutical formulation. Such formulation can be prepared by various technologies by a skilled person in the art. For example, the formulation can contain the therapeutic compound, a rate-controlling polymer (i.e., a material controlling the rate at which the therapeutic compound is released from the dosage form) and optionally other excipients. Some examples of rate-controlling polymers are hydroxy alkyl cellulose, hydroxypropyl alkyl cellulose (e.g., hydroxypropyl methyl cellulose, hydroxypropyl ethyl cellulose, hydroxypropyl isopropyl cellulose, hydroxypropyl butyl cellulose and hydroxypropyl hexyl cellulose), poly(ethylene)oxide, alkyl cellulose (e.g., ethyl cellulose and methyl cellulose), carboxymethyl cellulose, hydrophilic cellulose derivatives, and polyethylene glycol, compositions, e.g., those described in WO 2006/037342, incorporated herein by reference.

The pharmaceutical composition can be administered with or without food. In some embodiments, the pharmaceutical composition comprising the fumarate agent (e.g., DMF) is administered at least one hour before or at least one hour after food is consumed by the subject. In some embodiments, the pharmaceutical composition comprising the fumarate agent (e.g., DMF) is administered with food, for example, to reduce flushing.

In some embodiments, the neurological disorder is multiple sclerosis, wherein the first or second dose of the fumarate agent (e.g., DMF) is an amount that is effective in treating or preventing of multiple sclerosis, for example, in a subject who receives a vaccine before or during the first dosing period. For example, for DMF or MMF, the first or second dose can be a therapeutically effective amount range from about 1 mg/kg to about 50 mg/kg (e.g., from about 2.5 mg/kg to about 20 mg/kg or from about 2.5 mg/kg to about 15 mg/kg). Effective doses will vary, as recognized by those skilled in the art, dependent on route of administration, excipient usage, and the possibility of co-usage with other therapeutic treatments including use of other therapeutic agents.

In some embodiments, the first or second dose of DMF or MMF can be a therapeutically effective dose. In some embodiments, the therapeutically effective dose is a daily dose of from about 20 mg to about 1 g, for example, from about 100 mg to about 800 mg (e.g., from about 120 mg to about 720 mg, from about 240 mg to about 720 mg; or from about 480 mg to about 720 mg; or about 720 mg). The therapeutically effective dose of DMF or MMF can also be, for example, a daily dose of about 60 mg, about 80 mg, about 100 mg, about 120 mg, about 160 mg, about 200 mg, about 240 mg, about 320 mg, about 360 mg, about 400 mg, about 480 mg, about 600 mg, about 720 mg, about 800 mg, about 900 mg, about 1000 mg of DMF or MMF, or any ranges thereof. The dosages can be administered one or more times per day. For example, a 720 mg daily dose can be administered all at once or in separate administrations of 2, 3, 4, 5 or 6 (e.g., equal) doses. A 480 mg daily dose can be administered all at once or in separate administrations of 2, 3, 4, 5 or 6 (e.g., equal) doses. In some embodiments, the therapeutically effective dose of DMF or MMF is about 480 mg per day, effected by two equal, separate administrations, i.e., 240 mg per administration, at about 6 to about 12 hours apart in a day. In some embodiments, the therapeutically effective dose of DMF or MMF is about 720 mg per day, effected by three equal, separate administrations, i.e., 240 mg per administration, at about 4 to about 8 hours apart in a day. In some embodiments, the therapeutically effective dose of DMF or MMF is 300 mg to 1000 mg per day. In some embodiments, the therapeutically effective dose of DMF or MMF is 300 mg to 1000 mg per day delivered once daily. In some embodiments, the therapeutically effective dose of DMF or MMF is about 720 mg per day delivered once daily. In some embodiments, the therapeutically effective dose of DMF or MMF is about 480 mg per day delivered once daily.

In some embodiments, the first or second dose is administered to the subject by orally administering a dosage form that provides a total amount of about 60 mg to about 1000 mg of DMF. The dosage form can, for example, contain a total amount of DMF effective for treatment or prophylaxis of multiple sclerosis. The effective amount can range, but is not limited to, a total amount of about 60 mg to about 800 mg DMF, about 60 mg to about 720 mg DMF, 60 mg to about 500 mg DMF, about 60 mg to about 480 mg DMF, about 60 mg to about 420 mg DMF, about 60 mg to about 360 mg DMF, about 60 mg to about 240 mg DMF, about 60 mg to about 220 mg DMF, about 60 mg to about 200 mg DMF, about 60 mg to about 180 mg DMF, about 60 mg to about 160 mg DMF, about 60 mg to about 140 mg DMF, about 60 mg to about 120 mg DMF, about 60 mg to about 100 mg DMF, about 60 mg to about 80 mg DMF, about 80 mg to about 480 mg DMF, about 100 mg to about 480 mg DMF, about 120 mg to about 480 mg DMF, about 140 mg to about 480 mg DMF, about 160 mg to about 480 mg DMF, about 180 mg to about 480 mg DMF, about 200 mg to about 480 mg DMF, about 220 mg to about 480 mg DMF, about 240 mg to about 480 mg DMF, about 300 mg to about 480 mg DMF, about 360 mg to about 480 mg DMF, about 400 mg to about 480 mg DMF, about 450 mg to about 500 mg DMF, about 480 mg to about 500 mg DMF, about 80 to about 400 mg DMF, about 100 to about 300 mg DMF, about 120 to about 180 mg DMF, or about 140 mg to about 160 mg DMF.

The dosage form can contain, but is not limited to, a total amount of DMF of about 60 mg DMF, about 80 mg DMF, about 100 mg DMF, about 120 mg DMF, about 140 mg DMF, about 160 mg DMF, about 180 mg DMF, about 200 mg DMF, about 220 mg DMF, about 240 mg DMF, about 260 mg DMF, about 280 mg DMF, about 300 mg DMF, about 320 mg DMF, about 340 mg DMF, about 360 mg DMF, about 380 mg DMF, about 400 mg DMF, about 420 mg DMF, about 450 mg DMF, about 480 mg DMF, or about 500 mg DMF. In some embodiments, DMF is the only active ingredient in the dosage form.

In some embodiments, the fumarate agent is a compound that can be metabolized into MMF in vivo. And the first or second dose of the fumarate agent includes any amount of the compound that is equivalent to the amount of DMF or MMF described herein based on fumaric acid content.

In a healthy volunteer study, administration of 325 mg non-enteric coated aspirin 30 minutes prior to DMF dosing is found to reduce the occurrence and severity of flushing in the participating subjects. Subjects receiving a vaccine who experience flushing may be administered (e.g., 30 min. prior to DMF dosing) about 325 mg of aspirin to reduce flushing. Some patients who experience flushing with gastrointestinal side effects may reduce the dose to 120 mg DMF BID temporarily. Within a month, the effective dose of 240 mg DMF BID should be resumed.

In one embodiment, the method described herein further comprises administering to the subject one or more non-steroidal anti-inflammatory drugs (e.g., aspirin) before (for example, 10 minutes to an hour, e.g., 30 minutes before) administering the first or second dose of the pharmaceutical composition comprising the fumarate agent. In one embodiment, the subject administered the pharmaceutical composition comprising the fumarate agent takes the one or more non-steroidal anti-inflammatory drugs (e.g., aspirin) to reduce flushing. In another embodiment, the one or more non-steroidal anti-inflammatory drugs is selected from a group consisting of aspirin, ibuprofen, naproxen, ketoprofen, celecoxib, and combinations thereof. The one or more non-steroidal anti-inflammatory drugs can be administered in an amount of about 50 mg to about 500 mg before taking the dosage form described above. In one embodiment, a patient takes 325 mg aspirin before taking the pharmaceutical composition comprising the fumarate agent.

4.3.9 Immune Responses to the Vaccine

In any of the embodiments described herein, the subject can receive any type of vaccine (e.g., live or inactive vaccines). In a specific embodiment, the vaccine is a subunit vaccine. In some embodiments, the vaccine induces a T cell-dependent immune response (e.g., a T cell-dependent anamnestic humoral response, or a T cell-dependent primary response). In some embodiments, the vaccine induces a T cell-dependent anamnestic humoral immune response. In other embodiments, the vaccine induces a T cell-dependent neoantigen immune response.

In some embodiments, the vaccine induces an immune response against a virus, which can be, but is not limited to, adenovirus, arbovirus, coxsackievirus, cytomegalovirus, dengue virus, echinovirus, ebola virus, echovirus, enterovirus, hepatitis type A, hepatitis type B, hepatitis type C, herpes simplex virus type I (HSV-I), herpes simplex virus type II (HSV-II), human immunodeficiency virus type I (HIV-I), human immunodeficiency virus type II (HIV-II), hantavirus, influenza, measles virus, mumps virus, papillomavirus, papovavirus, polio virus, respiratory syncytial virus, rhinovirus, rinderpest, rotavirus, rubella virus, SARS coronavirus or varicella. In some embodiments, the vaccine induces an immune response against a bacterium of a genus, which can be, but is not limited to, *Chlamydia, Clostridium, Corynebacterium, Legionella, Mycobacterium, Mycoplasma, Neisseria, Rickettsia*, or *Streptococcus*. In a specific embodiment, the bacterium is *Clostridium tetani, Corynebacterium diphtheria, Neisseria meningitides*, or *Streptococcus pneumoniae*. In some embodiments, the vaccine induces an immune response against a protozoan of a genus, which can be, but is not limited to, *Kokzidioa, Leishmania*, or *Trypanosoma*.

In some embodiments, the vaccine induces a T cell-independent immune response (e.g., a Type 1 or Type 2 T cell-independent immune response). In some embodiments, the subject receives one vaccine that induces a T cell-dependent immune response and another vaccine that induces a T cell-independent immune response. In some embodiments, the subject receives a vaccines that has been approved by the U.S. Food and Drug Administration (FDA) or other corresponding foreign regulatory authorities. Non-limiting examples of FDA approved vaccines for use include those listed under the tradenames of Biothrax, BCG Vaccine, TICE BCG, Tripedia, Infanrix, DAPTACEL, Pediarix, KINRIX, Pentacel, PedvaxHIB, ActHIB, Hiberix, Comvax, Havrix, VAQTA, Twinrix, Recombivax HB, Engerix-B, Gardasil, Cervarix, Afluria, FluLaval, FluMist, Fluarix, Fluvirin, Agriflu, Fluzone, Fluzone High-Dose and Fluzone Intradermal, Flucelvax, Flublok, FluMist Quadrivalent, Fluarix Quadrivalent, Fluzone Quadrivalent, FluLaval, Quadrivalent, Ixiaro, JE-Vax, M-M-Vax, M-M-R II, ProQuad, MENVEO, MenHibrix, Menactra, Menomune-A/C/Y/W-135, Pneumovax 23, Prevnar, Prevnar 13, Poliovax, IPOL, Imovax, RabAvert, ROTARIX, RotaTeq, ACAM2000, DECAVAC, TENIVAC, Adacel, Boostrix, Vivotif, TYPHIM Vi, Varivax, YF-Vax, and Zostavax. In some embodiments, the vaccine is a tetanus diphtheria toxoids vaccine (e.g., TENIVAC). In some embodiments, the vaccine is a KLH vaccine. In some embodiments, the vaccine is PNEUMOVAX 23. In some embodiments, the vaccine is meningococcal polysaccharide diphtheria conjugate vaccine, quadrivalent (i.e., MCV4; e.g., MENVEO, which is Meningococcal [Groups A, C, Y and W-135] Oligosaccharide Diphtheria $CRM_{197}$ Conjugate Vaccine). In some embodiments, the vaccine is selected from the group consisting of tetanus diphtheria toxoids vaccine, keyhole limpet hemocyanin vaccine, pneumovax-23 vaccine, and any combinations thereof. In some embodiments, the vaccine is selected from the group consisting of tetanus diphtheria toxoids vaccine, pneumovax-23 vaccine, and meningococcal polysaccharide diphtheria conjugate vaccine (quadrivalent). In some embodiments, the subject receives more than one vaccine during the first dosing period. In one embodiment, the patient receives more than one vaccine on the same day. Suitable doses, routes of administration, and immunization schedules for the vaccine can be any of those according to a FDA approved label for the vaccine.

Immune responses of a subject to a vaccine can be measured by any method known to those skilled in the art. In some embodiments, the step of determining the immune response comprises obtaining serum antibody (e.g., IgG or IgM) levels in the subject induced by the vaccine post-immunization (e.g., 4 weeks after immunization), obtaining the serum antibody (e.g., IgG or IgM) levels in the subject pre-immunization, and comparing the serum antibody levels in the subject pre- and post-immunization. Methods for measuring serum antibody levels are known in the art. In some embodiments, the serum antibody level in the subject increases less than 4-fold (e.g., less than 3-fold or less than 2-fold) from pre-immunization to 4 weeks after immunization. In some embodiments, the serum antibody level in the subject increases at least 2-fold (e.g., at least 4-fold or at least 10-fold) from pre-immunization to 4 weeks after immunization. In some embodiments, the serum antibody is IgG against tetanus diphtheria toxoids, keyhole limpet hemocyanin, or pneumovax-23, and the serum IgG level in the subject increases less than 4-fold (e.g., less than 3-fold or less than 2-fold) from pre-vaccination to 4 weeks after vaccination. In some embodiments, the serum IgG level in the subject increases at least 2-fold (e.g., at least 4-fold or at least 10-fold) from pre-immunization to 4 weeks after immunization.

In some embodiments, the immune response of the subject to the vaccine is characterized in that the serum antibody level in the subject increases at least 2-fold (e.g., at least 4-fold or at least 10-fold) from pre-immunization to 4 weeks after immunization, and the second dose is the same as the first dose. In some embodiments, the serum antibody is IgG against tetanus diphtheria toxoids, keyhole limpet hemocyanin, or pneumovax-23.

In some embodiments, the first dose is a daily dose of about 480 mg or about 720 mg of DMF divided into 1, 2, or 3 (e.g., equal) doses. In some embodiments, the second dose is a daily dose of about 120 mg, about 240 mg, or about 360 mg divided into 1, 2, or 3 (e.g., equal) doses. In some embodiments, the second dose is 0 mg fumarate agent. In some embodiments, the subject is administered the same amount of fumarate agent as in the first dosing period after the second dosing period.

4.4 Method 2. Screening for Lower Risk Dose

In some embodiments, the invention also provides a method of treating or preventing a disease or disorder (e.g., as described herein) in a subject who receives a vaccine, comprising screening a plurality of doses of a pharmaceutical composition comprising a fumarate agent selected from the group consisting of monomethyl fumarate, a compound that metabolizes into monomethyl fumarate in vivo, a deuterated analog thereof, a pharmaceutically acceptable salt thereof, and a combination thereof, by (1) identifying a first group of subjects and at least a second group of subjects, wherein both the first and second groups of subjects receive a vaccine, wherein the first group of subjects is treated with a first dose of the pharmaceutical composition, and the second group of subjects is treated with a second dose of the pharmaceutical composition; and (2) determining a lower risk dose. In some embodiments, the method further comprises administering the lower risk dose of the pharmaceutical composition to the subject.

Methods for determining a lower risk dose of the pharmaceutical composition are known. In some embodiments, the lower risk dose is determined by comparing immune responses to the vaccine between the first and second groups of subjects, and the group of subjects treated with the lower risk dose have higher proportion of subjects with at least 2-fold increase in scrum antibody levels induced by the vaccine from pre-vaccination to 4 weeks after vaccination. In some embodiments, the group of subjects treated with the lower risk dose have higher proportion of subjects having serum antibody levels induced by the vaccine not less than average serum antibody level observed in subjects administered with the vaccine but no fumarate agent at 4 weeks after vaccination.

Methods for determining a lower risk dose can also include comparing adverse effects observed between the first and second groups of subjects. In some embodiments, the group of subjects treated with the lower risk dose have a lower rate of a particular adverse effect (e.g., decreased incidence of headache, flushing, gastrointestinal event, or infection).

In some embodiments, the invention provides a method of treating or preventing multiple sclerosis in a subject in need thereof, comprising (a) determining a subject's baseline lymphocyte count prior to treatment;

(b) administering to the subject a first dose of a pharmaceutical composition for a first dosing period, wherein the pharmaceutical composition comprises a fumarate agent selected from the group consisting of monomethyl fumarate, a compound that metabolizes into monomethyl fumarate in vivo, a deuterated analog thereof, a pharmaceutically acceptable salt thereof, and a combination thereof;

(c) determining a subject's total lymphocyte count after the first dosing period; and (d) if the lymphocyte count after the first dosing period is 90% of the baseline lymphocyte count or lower, do not administer tetanus diphtheria toxoids vaccine, keyhole limpet hemocyanin vaccine, pneumovax-23 vaccine, or any combinations thereof.

In some embodiments, the lymphocyte count after the first dosing period is about 10% to about 90% of the baseline lymphocyte count. In some embodiments, the lymphocyte count is about 10% to about 80% of the baseline lymphocyte count. In some embodiments, the lymphocyte count is about 10% to about 70% of the baseline. In some embodiments, the lymphocyte count is about 10% to about 50% of the baseline. In some embodiments, the lymphocyte count after the first dosing period is about 20% to about 90% of the baseline lymphocyte count. In some embodiments, the lymphocyte count is about 20% to about 80% of the baseline lymphocyte count. In some embodiments, the lymphocyte count is about 20% to about 70% of the baseline lymphocyte count. In some embodiments, the lymphocyte count is about 20% to about 60% of the baseline lymphocyte count. In some embodiments, the lymphocyte count is about 20% to about 50% of the baseline lymphocyte count. In some embodiments, the lymphocyte count is about 30% to about 90% of the baseline lymphocyte count. In some embodiments, the lymphocyte count is about 30% to about 80% of the baseline lymphocyte count. In some embodiments, the lymphocyte count is about 30% to about 70% of the baseline lymphocyte count. In some embodiments, the lymphocyte count is about 30% to about 60% of the baseline lymphocyte count. In some embodiments, the lymphocyte count is about 40% to about 90% of the baseline lymphocyte count. In some embodiments, the lymphocyte count is about 40% to about 80% of the baseline lymphocyte count. In some embodiments, the lymphocyte count is about 40% to about 70 of the baseline lymphocyte count. In some embodiments, the lymphocyte count is about 40% to about 70 of the baseline lymphocyte count. In some embodiments, the lymphocyte count is about 40% to about 60% of the baseline lymphocyte count. In some embodiments, the lymphocyte count is about 40% to about 50% of the baseline lymphocyte count. In some embodiments, the lymphocyte count after the first dosing period is about 10%, about 15%, about 20%, about 25%, about 30%, about 35, about 40%, about 50%, about 55%, about 60%, about 65%, about 70%, about 75%, about 80%, about 85%, or about 90% of the baseline lymphocyte count.

Suitable fumarate agents, first and second doses of the pharmaceutical composition, vaccines, methods for determining immune responses to the vaccines, and diseases or disorders can be those described herein for Method 1.

The following examples are illustrative and do not limit the scope of the claimed embodiments.

5. EXAMPLES

5.1 Example 1: A Randomized, Open-Label Study to Assess the Effects of BG00012 on the Immune Response to Vaccination and on Lymphocyte Subsets in Subjects with Relapsing Forms of Multiple Sclerosis

5.1.1 Introduction

The primary objective of the study is to evaluate the effects of DMF administered over approximately 6 months on immune responses to vaccination with tetanus diphtheria toxoids vaccine (Td) [T cell-dependent anamnestic humoral response] and keyhole limpet hemocyanin (KLH) [T cell-dependent neoantigen response] in subjects with relapsing forms of MS.

Secondary objectives of this study in this study population are as follows: (1) to evaluate the effects of DMF administered over approximately 6 months on the immune response to vaccination with pneumovax-23 (PPSV23) [a mostly T cell-independent humoral response]; (2) to evaluate the pharmacodynamic effects of DMF on lymphocyte subtypes over 1 year of treatment; (3) to evaluate the pharmacodynamic effect of DMF on immunoglobulin levels over time; and (4) to evaluate the safety and tolerability of DMF.

5.1.2 DMF and Vaccines for the Study

DMF is a drug product formulated as enteric-coated microtablets in gelatin capsules (blue and white) for oral administration. Each capsule contains 120 mg DMF. Excipients for the manufacturing of the enteric-coated microtablets include microcrystalline cellulose, croscarmellose sodium, talc, colloidal anhydrous silica (colloidal silicon dioxide), magnesium stearate, triethyl citrate, methacrylic acid-methyl methacrylate copolymer, methacrylic acid-ethyl acrylate copolymer, simethicone, sodium lauryl sulfate, and polysorbate 80. Excipients for the manufacturing of the capsule shell include gelatin, titanium dioxide, and indigotin.

Tetanus diphtheria toxoids vaccine (Td [Tenivac®]; Sanofi Pasteur, Swiftwater, Pa.) is indicated for active immunization for the prevention of tetanus and diphtheria. It is used in this study to assess the integrity of a T cell-dependent anamnestic humoral response, as tetanus toxoid is an immunogen commonly administered to the general population.

Keyhole limpet hemocyanin (KLH) is used to test the integrity of a T cell-dependent primary response, as it is a novel immunogen for most individuals. KLH is administered as Immucothel® (Biosyn Arzneimittel AG, Fellbach, Germany), a hemocyanin product derived from KLH, which is obtained from the sca snail giant keyhole limpet. Immucothel is approved for treatment of bladder cancer in several countries and is considered an investigational agent in the US, where it is used in clinical studies to produce an immune response.

Pneumovax® 23 (PPSV23; Merck & Co., Inc., Rahway, N.J., USA) is a 23-valent carbohydrate antigen vaccine approved for the prophylaxis of community-acquired pneumonia. Pneumococcal polysaccharide antigens are able to activate B cells without T cell help, and thus are considered type 2 T cell independent antigens. However, they are also able to induce an adaptive humoral immune response, due to a secondary signal of B cell activation provided by other immune cells and with some T cell involvement. PPSV23 is therefore be used in this study to assess a mostly T cell-independent humoral response.

5.1.3 Dosage Selection

The DMF dosage selected for this study (120 mg twice daily [BID] for the first week, 240 mg BID thereafter) is the approved DMF dosing regimen in patients with relapsing forms of MS in the United States (US).

Td (0.5 mL) and PPSV23 (0.5 mL) doses selected for this study are the current approved doses for these vaccines. KLH (1 mg) is the subcutaneous (SC) injection dose based on Immucothel Investigator's Brochure.

Subjects with relapsing forms of MS between the ages of 18 and 55 years, with a known history of tetanus immunization.

5.14 Inclusion/Exclusion Criteria

Exemplary eligibility criteria at randomization include: (1) Male and female subjects of childbearing potential will practice effective contraception during the study and be willing and able to continue contraception for 30 days after their last dose of study treatment; (2) Aged 18 to 55 years old, inclusive, at the time of informed consent; (3) a confirmed diagnosis of a relapsing form of MS; and (4) a known history of tetanus immunization.

Exemplary exclusion criteria at randomization include: (1) Tetanus vaccination given less than 2 years or more than 15 years prior to Screening, or an anti-tetanus IgG titer at Screening that is greater than one-half the upper limit of detection for the assay; (2) Pneumococcal vaccination within the S years prior to Screening; (3) Previous exposure to KLH or vaccines containing KLH components (e.g., cancer vaccines); (4) Known hypersensitivity to KLH, PPSV23, or tetanus/diphtheria toxoids or any other administered vaccinations or their components (e.g., thimerosol); (5) Known allergy to shellfish; (6) History of, or positive test result at Screening for hepatitis C virus (HCV) antibody or hepatitis B virus (defined as positive for hepatitis B surface antigen [HBsAg] or hepatitis B core antibody [HBcAb]); (7)

History of human immunodeficiency virus (HIV); (8) History of drug or alcohol abuse (as defined by the Investigator) within 2 years prior to Screening; (9) Current smoking or smoking within 6 months prior to Screening; (10) Any clinically significant (in the judgment of the Investigator) infectious illness (e.g., cellulitis, abscess, pneumonia, septicemia) within 30 days prior to Screening; (11) Any active bacterial or viral infection (as assessed by the Investigator) at randomization; (12) History of clinically significant (in the judgment of the Investigator) cardiovascular, dermatologic, endocrinologic, gastrointestinal, hematologic, hepatic, immunologic, metabolic, neurologic (other than MS), psychiatric, pulmonary, renal, urologic, and/or other major disease that would preclude participation in a clinical trial; (13) History of malignancy (subjects with basal cell carcinoma that has been completely excised prior to study entry remain eligible); (14) History of severe allergic or anaphylactic reactions or known drug hypersensitivity; (15) Any of the following abnormal blood tests at Screening that are confirmed on repeat testing 2 weeks later: (a) alanine transaminase/serum glutamate-pyruvate transaminase (ALT/SGPT), or aspartate transaminase/serum glutamic-oxaloacetic transaminase (AST/SGOT), or gamma-glutamyltransferase (GGT) ≥22 times the upper limit of normal (ULN); (b) leukocytes <3500/mm$^3$; and (c) eosinophils >0.7×10$^3$/μL or >0.7 GI/L; (16) Any of the following abnormal urine tests at Screening confirmed by a second urinalysis 2 weeks later: (a) proteinuria (1+ or greater); (b) hematuria, without known etiology; (c) glycosuria, without known etiology; (17) Any previous treatment with Fumaderm® or DMF (FAG-201); (18) Any type of live vaccine within 4 weeks prior to randomization, including but not limited to measles/mumps/rubella vaccine, varicella zoster virus vaccine, oral polio vaccine, and nasal influenza vaccine; (19) Prior treatment with any of the following: cladribine, mitoxantrone, fingolimod, alemtuzumab, total lymphoid irradiation, T-cell or T-cell receptor vaccination, any therapeutic monoclonal antibody, with the exception of Tysabri® (natalizumab) (see exclusion #20); (20) Treatment with Tysabri (natalizumub) within 1 year prior to randomization; (21) Treatment with any of the following medications or procedures within the 6 months prior to randomization: cyclosporine, azathioprine, teriflunomide, methotrexate, mycophenolate mofetil, intravenous immunoglobulin, plasmapheresis or cytapheresis; (22) Treatment with any of the following within 2 weeks prior to randomization: subcutaneous or oral glatiramer acetate, interferon-α, interferon-β; (23) Treatment with any of the following within 4 weeks prior to randomization: Steroids (intravenous [IV] or oral corticosteroid treatment, including agents that may act through the corticosteroid pathway [e.g., low dose naltrexone]), 4-aminopyridine or related products; and (24) Treatment with another investigational drug or approved therapy for investigational use within the 6 months prior to randomization.

5.1.5 Endpoints

The primary end points of this study are (1) the proportion of subjects with a ≥2-fold rise in anti-tetanus serum immunoglobulin G (IgG) levels from pre-vaccination to 4 weeks after Td vaccination; and (2) The proportion of subjects with a ≥2-fold rise in anti-KLH serum IgG levels from pre-vaccination to 4 weeks after the final KLH vaccination.

Secondary end points for this study are (1) the proportion of subjects with a ≥4-fold rise in anti-tetanus serum IgG levels from pre-vaccination to 4 weeks after Td vaccination; (2) the proportion of subjects with a ≥4-fold rise in anti-KLH serum IgG levels from pre-vaccination to 4 weeks after the final KLH vaccination; (3) the proportion of subjects with a ≥2- and a ≥4-fold rise in anti-pneumococcal IgG levels from pre-vaccination baseline to 4 weeks after PPSV23 vaccination; (4) Anti-tetanus, anti-KLH, and anti-pneumococcal immunoglobulin levels over time; (5) Change over time in lymphocyte subsets, including: T cells, B cells, NK cells (e.g., Total T cells: CD4+/CD8+; Total B cells; Total NK); (6) Additional analysis of lymphocyte subsets which can include: Treg Panel (total Treg, Resting/naïve Treg; and/or active Treg); T-cell panel (Naïve; Effector; Central/Effector Memory; and/or Activated (expressing HLA-DR/CD38)); (7) Myeloid NK panel (Monocytes: CD16+ (non-classical)/CD16− (classical); Dendritic cells: myeloid/plasmacytoid; and/or NKs: CD56$^{dim}$/CD56$^{bright}$); B cell panel (Translational; Naïve; Memory: IgD+/IgD−; and/or Plasmablast); and (8) Safety parameters, including incidence of all AEs, including those leading to treatment discontinuation and study withdrawal, and all serious adverse events (SAEs); clinical laboratory shifts in reported values; and clinically significant changes in vital sign measurements.

In addition, Ribonucleic acid (RNA) and peripheral blood mononuclear cells (PBMCs) are collected in certain subjects evaluate lymphocyte subsets. PBMCs are separated and frozen for testing at a later time at the Sponsor's discretion.

5.1.6 Treatment Schedule

Approximately 68 subjects are enrolled in the study. Subjects are randomized in a 1:1 ratio to Group 1 (DMF treatment plus immunizations) or Group 2 (immunizations alone).

Group 1 subjects are treated with DMF 120 mg BID for first 7 days and 240 mg BID thereafter up to 48 weeks. Table 1 shows a detailed schedule of events for Group 1 subjects.

At Week 24, subjects in Group 1 receive Td, PPSV23, and KLH vaccinations. At 2 and 4 weeks after the Week 24 vaccination, subjects receive an additional KLH vaccination (Weeks 26 and 28). Anti-tetanus and anti-pneumococcal IgG titers are measured just prior to and at 4 and 8 weeks after the Week 24 vaccinations (i.e., Weeks 24, 28, and 32). Anti-KLH IgG titers are measured just prior to and at 4, 8, and 12 weeks after the Week 24 vaccination (i.e., Weeks 24, 28, 32, and 36). (Anti-tetanus titers are also measured at Screening, as part of the eligibility criteria). Blood samples for lymphocyte subset analysis, as well as blood samples for determination of each subject's complete blood count (CBC) with differential, are collected at Screening, Baseline (Day 1), and Weeks 12, 24, 36, and 48. Clinical samples for analysis of blood chemistries and urinalysis are collected at Screening and at Weeks 24 and 48. A serum pregnancy test is performed at Screening, as part of the eligibility criteria. Urine pregnancy tests are performed at Baseline (Day 1), and Weeks 12, 24, 26, 28, 32, 36, and 48. Vital signs, AEs, and concomitant therapies are assessed at every clinic visit. A final follow-up clinic visit at which safety assessments are performed occurs 4 weeks after the final dose of DMF in subjects who do not continue treatment with commercial DMF. Subjects who plan to continue treatment with commercial DMF after Week 48 are contacted by telephone 2-4 weeks after their last study dose to ensure transition has taken place. If for any reason they have not started commercial DMF, they are required to have a final follow-up clinic visit 4 weeks after their last study dose.

Group 2 subjects receive the same vaccinations and assessments over a 12-week period according to the schedule in Group 1, but with vaccinations starting on Day 1. That is, subjects receive Td, PPSV23, and KLH vaccinations at Baseline (Day 1) and an additional KLH vaccination at Weeks 2 and 4. Anti-tetanus and anti-pneumococcal IgG titers are measured just prior to and at 4 and 8 weeks after Baseline (Day 1). Anti-KLH IgG titers are measured just prior to and at 4, 8, and 12 weeks after the Day vaccination. (Anti-tetanus titers are also measured at Screening, as part of the eligibility criteria). Blood samples for lymphocyte subset analysis (as well as CBC with differential for laboratory safety analysis) are collected at Screening, Baseline (Day 1), and Week 12. Clinical samples for analysis of blood chemistries and urinalysis are collected at Screening and Week 12 and at Screening, Baseline (Day 1), and Week 12, respectively. A serum pregnancy test is performed at Screening, as part of the eligibility criteria. Urine pregnancy tests are performed at Baseline (Day 1), and Weeks 2, 4, and 12. Vital sign measurements, AEs, and concomitant therapies are performed at every clinic visit. After completing the study, Group 2 subjects may be eligible to begin treatment with commercial DMF if deemed appropriate. Table 2 shows a detailed schedule of events for Group 2 subjects.

Subjects randomized to Group 1 (DMF treatment plus immunizations) have 9 clinic visits: Screening, Baseline (Day 1), and Weeks 12, 24, 26, 2H, 32, 36, and 4H. Subjects who do not continue treatment with commercial DMF after Week 48 have a final follow-up clinic visit 4 weeks after the final dose. Subjects who plan to continue treatment with commercial DMF after Week 48 are contacted by telephone 2-4 weeks after their last study dose to ensure transition has taken place. If for any reason they have not started commercial DMF they are required to have a final follow-up clinic visit 4 weeks after their last study dose.

Subjects randomized to Group 2 (immunizations alone) have 6 clinic visits: Screening, baseline (Day 1), and Weeks 2, 4, 8, and 12.

5.1.7 Efficacy Analysis

Analysis of the primary endpoint for the Td and KLH vaccinations is based on evaluable subjects (i.e., subjects who are appropriately vaccinated per protocol; are ≥70% compliant with DMF [Group 1 only], and have non-missing IgG levels at pre-vaccination and 4 weeks after final vaccination).

TABLE 1

| Group 1 Schedule of Events | | | | | | | | | |
|---|---|---|---|---|---|---|---|---|---|
| Tests and Assessments[1] | Screening (w/in 28 days before Baseline) | Baseline (Day 1) | Week 12 (Day 84 ± 3 days) | Week 24 (Day 168 ± 3 days) | Week 26 (Day 182 ± 3 days) | Week 28 (Day 196 ± 3 days) | Week 32 (Day 224 ± 3 days) | Week 36 (Day 252 ± 3 days) | Week 48 (Day 336 ± 3 days)/W/D[2] | Follow-Up (4 weeks ± 5 days after final dose)[2] |
| Informed consent[3] | X | | | | | | | | | |
| Medical history | X | | | | | | | | | |
| Physical examination | X | | | | | | | | X | |
| Vital signs[4] | X | X | X | X | X | X | X | X | X | X |
| Hepatitis B and C screen | X | | | | | | | | | |
| Hematology (CBC with differential) | X | X | X | X[5] | | | | X | X | X |
| Blood chemistry | X | | | X[5] | | | | | X | X |
| Urinalysis | X | | | X[5] | | | | | X | X |
| Serum pregnancy test[6] | X | | | | | | | | | |
| Urine pregnancy test[6] | | X | X | X | X | X | X | X | X | |
| Dispense DMF | | X | X | X | | X | X | X | | |
| DMF administration | | DMF is to be taken as 120 mg BID for the first 7 days and thereafter as 240 mg BID. Subjects are to be instructed to take DMF orally, by swallowing the capsules whole without chewing, and with or without food. | | | | | | | | |
| Tetanus toxoid vaccine[7] | | | | X | | | | | | |
| PPSV23 vaccine[7] | | | | X | | | | | | |
| Anti-tetanus and anti-pneumococcal antibody assays | Anti-tetanus only | | | X[5] | | | X[5] | X | | |
| KLH vaccine[7] | | | | X | X | X | | | | |
| KLH antibody assay | | | | X[5] | | X[5] | X | X | | |
| Lymphocyte subset analysis | X | X | X | X[5] | | | | X | X | X |
| Concomitant therapy and procedures | X | X | X | X | X | X | X | X | X | X |
| SAE recording | X | X | X | X | X | X | X | X | X | X |
| AE recording | | X | X | X | X | X | X | X | X | X |

TABLE 1-continued

Group 1 Schedule of Events

| Tests and Assessments[1] | Screening (w/in 28 days before Baseline) | Baseline (Day 1) | Week 12 (Day 84 ± 3 days) | Week 24 (Day 168 ± 3 days) | Week 26 (Day 182 ± 3 days) | Week 28 (Day 196 ± 3 days) | Week 32 (Day 224 ± 3 days) | Week 36 (Day 252 ± 3 days) | Week 48 (Day 336 ± 3 days)/W/D[2] | Follow-Up (4 weeks ± 5 days after final dose)[2] |
|---|---|---|---|---|---|---|---|---|---|---|
| RNA collection[8] | | X | X | X[5] | | | | X | X | X |
| PBMC collection[8] | | X | | X[5] | X | | | | X | |

[1]All tests and assessments will be performed before dispensing study treatment.
[2]Subjects who discontinue treatment prematurely are withdrawn from the study and have a Withdrawal visit within 4 weeks after taking their final study dose. Subjects who do not continue treatment with commercial DMF after Week 48/early withdrawal have a final follow-up clinic visit 4 weeks after their final study dose. Subjects who plan to continue treatment with commercial DMF after Week 48 are contacted by telephone 2-4 weeks after their last study dose to ensure transition has taken place. If for any reason they have not started commercial DMF they are required to have a final follow-up clinic visit 4 weeks after their last study dose.
[3]Written informed consent will be obtained prior to performing any study-related procedures, and may be obtained prior to Screening if a washout period is required for prior therapy.
[4]Vital signs include height (measured at Screening only), weight, diastolic and systolic blood pressure, heart rate, and temperature. Subjects will be seated for 5 minutes prior to having their pulse and blood pressure measured.
[5]Blood as well as urine samples will be collected prior to immunization.
[6]Females of childbearing potential only. Results will be known to be negative prior to dispensing DMF and immunization.
[7]Subjects are observed for any severe local or systemic reactions for 45 minutes following immunization.
[8]RNA and PBMC are collected in subjects who have signed a separate Future Scientific Research informed consent form.

TABLE 2

Group 2 Schedule of Events

| Tests and Assessments[1] | Screening (within 28 days before Baseline) | Baseline (Day 1) | Week 2 (Day 14 ± 3 days) | Week 4 (Day 28 ± 3 days) | Week 8 (Day 56 ± 3 days) | Week 12 (Day 84 ± 3 days)/W/D[2] |
|---|---|---|---|---|---|---|
| Informed consent[3] | X | | | | | |
| Medical history | X | | | | | |
| Physical examination | X | | | | | |
| Vital signs[4] | X | X | X | X | X | X |
| Hepatitis B and C screen | X | | | | | |
| Hematology (CBC with differential) | X | X[5] | | | | X |
| Blood chemistry | X | | | | | X |
| Urinalysis | X | X[5] | | | | X |
| Serum pregnancy test[6] | X | | | | | |
| Urine pregnancy test[6] | | X | X | X | | X |
| Tetanus toxoid vaccine[7] | | X | | | | |
| PPV23 vaccine[7] | | X | | | | |
| Anti-tetanus and anti-pneumococcal antibody assays | Anti-tetanus only | X[5] | | X[5] | X | |
| KLH vaccine[7] | | X | X | X | | |
| KLH antibody assay | | X[5] | | X[5] | X | X |
| Lymphocyte subset analysis | X | X[5] | | | | X |
| Concomitant therapy and procedures | X | X | X | X | X | X |
| SAE recording | X | X | X | X | X | X |
| AE recording | | X | X | X | X | X |
| RNA collection[8] | | X[5] | | | | |
| PBMC collection[8] | | X[5] | X | | | |

[1]All tests and assessments will be performed prior to immunization.
[2]In subjects who are withdrawn from the study, a Withdrawal Visit is performed within 4 weeks after their last immunization.
[3]Written informed consent will be obtained prior to performing any study-related procedures, and may be obtained prior to Screening if a washout period is required for prior therapy.
[4]Vital signs include height (measured at Screening only), weight, diastolic and systolic blood pressure, heart rate, and temperature. Subjects will be seated for 5 minutes prior to having their pulse and blood pressure measured.
[5]Blood as well as urine samples will be collected prior to immunization.
[6]Females of childbearing potential only. Results will be known to be negative prior to immunization.
[7]Subjects are observed for any severe local or systemic reactions for 45 minutes following immunization.
[8]RNA and PBMC are collected in subjects who have signed a separate Future Scientific Research informed consent form.

5.2 Example 2: An Open-Label Study to Assess the Immune Response to Vaccination in Tecfidera® (BG000121)-Treated Versus Interferon-Treated Subjects with Relapsing Forms of Multiple Sclerosis

5.2.1 List of Abbreviations

The following abbreviations and definitions are used in this study protocol:

| | |
|---|---|
| AE | adverse event |
| BID | twice daily |
| CI | confidence interval |
| CRF | case report form |
| EDC | electronic data capture |
| GCP | Good Clinical Practice |
| ICF | informed consent form |
| ICH | International Conference on Harmonisation |
| IFN | interferon |
| IgG | immunoglobulin G |
| MCV4 | meningococcal polysaccharide diphtheria conjugate vaccine (quadrivalent) |
| MS | multiple sclerosis |
| PHI | protected health information |
| PPSV23 | 23-valent pneumococcal polysaccharide vaccine |
| RRMS | relapsing-remitting multiple sclerosis |
| SAE | serious adverse event |
| SUSAR | suspected unexpected serious adverse reaction |
| Td | tetanus diphtheria toxoids vaccine |
| US | United States |

5.2.2 Synopsis

This is a brief summary of the study protocol.

Existing Multiple Sclerosis Treatment (Not Supplied by the Sponsor) include Tecfidera® (dimethyl fumarate) and non-pegylated interferon (IFN; e.g., Avonex®, Betaseron®, Rebif®, Extavia®).

5.2.2.1. Study Objectives

Primary

The primary objective of the study is to evaluate the immune response to vaccination with Td in subjects with relapsing forms of MS who have been treated with Tecfidera versus those treated with non-pegylated IFN.

Secondary

The secondary objective of the study is to evaluate the immune response to vaccination with PPSV23 and MCV4.

5.2.2.2. Study Endpoints

Primary

The primary endpoint of the study is:

The proportion of subjects with a ≥2-fold rise in anti-tetanus serum immunoglobulin G (IgG) levels from pre-vaccination to 4 weeks after Td vaccination.

Secondary

The secondary endpoints of the study are:

The proportion of subjects with a ≥4-fold rise in anti-tetanus serum IgG levels from pre-vaccination to 4 weeks after Td vaccination.

The proportion of subjects with a ≥2-fold and a ≥4-fold rise in anti-pneumococcal serum IgG levels against serotypes 3 and 8 from pre-vaccination to 4 weeks after PPSV23 vaccination.

The proportion of subjects with a ≥2-fold and a ≥4-fold rise in anti-meningococcal serum IgG levels against serotype C from pre-vaccination to 4 weeks after MCV4 vaccination.

The geometric mean titer ratios from pre-vaccination to 4 weeks after Td, PPSV23, and MCV4 vaccinations.

Incidence of adverse events (AEs) and serious adverse events (SAEs).

Clinical laboratory shifts in reported values.

Clinically significant changes in vital sign measurements.

Exploratory

The exploratory endpoints of the study are:

The proportion of subjects with a ≥2-fold and a ≥4-old rise in anti-diphtheria toxoid serum IgG levels from pre-vaccination to 4 weeks after MCV4 vaccination.

The anti-diphtheria geometric mean titer ratio from pre-vaccination to 4 weeks after MCV4 vaccination.

The proportion of subjects with anti-tetanus and anti-meningococcal seroprotective levels at 4 weeks after Td and MCV4 vaccinations.

5.2.2.3. Study Design

This is an open-label, multicenter study to evaluate the immune response to vaccination in subjects with relapsing forms of MS who have been treated for at least 6 months with the approved dose of Tecfidera (240 mg twice daily [BID]) or who have been treated for at least 3 months with the approved dose of a non pegylated IFN (e.g., Avonex, Betaseron, Rebif, Extavia).

After a 28-day Screening Period, eligible subjects will be enrolled and assigned as appropriate into either Group 1 (currently treated with Tecfidera) or Group 2 (currently treated with non-pegylated IFN). Throughout the study, subjects will remain on their existing, stable dosing regimen of Tecfidera or non pegylated IFN.

Subjects will come to the clinic on Day 1 and have blood samples drawn for pre vaccination anti-tetanus, anti pneumococcal, anti meningococcal, and anti-diphtheria IgG titers. All subjects will receive 3 vaccinations: Td, PPSV23, and MCV4. They will return to the clinic at Week 4 for their final study visit, at which time blood samples will be drawn for post-vaccination IgG titers.

Subjects who receive at least 1 dose of a vaccine should remain in the study and attend the Week 4 Visit. Subjects who receive at least 1 dose of a vaccine but would like to withdraw from the study prematurely will be asked to return to the clinic for an Early Withdrawal Visit, at which time blood samples will be drawn for IgG titers.

Safety evaluations in this study will include blood samples for complete blood count with differential and blood chemistry, urine pregnancy tests, and vital signs at Day 1 and Week 4, as well as ongoing collection of AEs, SAEs, and concomitant medications.

The subjects' neurologist or primary healthcare provider will manage their MS care before, during, and after study participation.

This study will be conducted at approximately 10 to 15 sites in the United States, and the number of planned subjects will be 70 (approximately 35 in each group)

5.2.2.4. Study Population

Subjects with relapsing forms of MS between the ages of 18 and 55 years, inclusive, with a known history of tetanus immunization and on a stable approved dose of either Tecfidera (240 mg BID) for ≥6 months or a non pegylated IFN for ≥3 months.

5.2.2.5. Treatment Groups

Subjects treated with Tecfidera will be assigned to Group 1. Subjects treated with non pegylated IFN will be assigned to Group 2.

All subjects will receive the same 3 vaccinations on Day 1 intramuscularly in the specified order:
1. Td 0.5 mL
2. PPSV23 0.5 mL
3. MCV4 0.5 mL

5.2.2.6. Study Duration

Subjects will have 3 clinic visits: Screening, Day 1, and Week 4. The duration of study participation will be approximately H weeks.

5.2.2.7. Criteria for Evaluation

Efficacy
Anti-tetanus, anti pneumococcal, anti meningococcal, and anti-diphtheria IgG levels at pre vaccination (Day 1) and at Week 4
Safety
The following safety assessments will be performed:
Vital sign measurements
Physical examination
Hematology and blood chemistry
Serum and urine pregnancy testing
Monitoring and recording of AEs
Monitoring and recording of concomitant therapy and procedures

5.2.2.8. Statistical Methods

No formal statistical testing is planned. The proportion of responders to each vaccine antigen will be estimated with 95% confidence intervals (CIs) using the exact method. Differences in the proportion of subjects with an antibody response between Group 1 and Group 2 will also be estimated with 95% CIs using the exact method. The IgG level to each antigen will also be summarized by geometric mean concentration for each group with 95% CI as well as the ratio between the 2 groups.

All safety data will be summarized using descriptive statistics. Incidence of AEs will be summarized using frequency distribution tables by group, overall, by severity, and by relationship to vaccines. Change from baseline in laboratory values and vital signs will also be descriptively summarized by group.

No interim analysis will be performed.

5.2.2.9. Sample Size Determination

The sample size for this study is not based on formal hypothesis testing, but on the precision of estimated response rates. The 95% CIs for the difference between Groups 1 and 2 in the proportion of vaccination responders will be provided to quantify the variability in the differences of response rates.

Assuming a response rate of 95% to Td in Group 2 (the reference group) and a range of hypothetical response rates in Group 1 (the test group), an evaluable size of 32 subjects per group would provide the following 95% CIs for the difference between groups (Group 1-Group 2) in the proportion of vaccination responders:

| Group 1 Response Rate | Difference (Group 1 − Group 2) | 95% CI for the Difference |
|---|---|---|
| 95% | 0 | [−13.8%, 13.8%] |
| 75% | −20% | [−39.9%, 0.1%] |
| 70% | −25% | [−45.7%, −4.3%] |
| 65% | −30% | [−51.3%, −8.7%] |
| 55% | −40% | [−61.9%, −18.1%] |

The analysis population for the primary endpoint of ≥2-fold rise in anti-tetanus serum IgG levels comprises subjects who are appropriately vaccinated per protocol, have not taken any concomitant medication that could impact immune responses, and who have nonmissing pre-vaccination and post vaccination IgG levels with a pre-vaccination level less than or equal to one half the upper limit of detection for the assay. It is anticipated that a total sample size of approximately 70 subjects (35 subjects per group) will need to be enrolled in order to obtain a total of 64 evaluable subjects (32 subjects per group). The sample size determination takes into account an approximate 10% loss of evaluable subjects.

5.2.3 Schedule of Events

TABLE 3

Schedule of Events

| Tests and Assessments | Screening (Within 28 days Before Day 1) | Day 1 | Week 4 (Day 28 ± 3 days) or Early Withdrawal |
|---|---|---|---|
| Informed Consent[1] | X | | |
| Inclusion/Exclusion Criteria | X | X | |
| Medical History | X | | |
| Vital Signs[2] | X | X | X |
| Physical Examination | X | | |
| Hematology (CBC With Differential) | X | X[3] | X |
| Blood Chemistry | X | X[3] | X |
| Pregnancy Tests[4] | Serum | Urine | Urine |
| Blood Collection for Anti-Tetanus, Anti-Pneumococcal | Anti-Tetanus Only | X[3] | X |

TABLE 3-continued

Schedule of Events

| Tests and Assessments | Screening (Within 28 days Before Day 1) | Day 1 | Week 4 (Day 28 ± 3 days) or Early Withdrawal |
|---|---|---|---|
| Anti-Meningococcal, and Anti-Diphtheria IgG Titers | | | |
| Vaccines Td[5] | | X | |
| PPSV23[5] | | X | |
| MCV4[5] | | X | |
| SAE and Concomitant Therapy and Procedures Recording | X ---------------------------------------------------------- X | | |
| AEs Recording | | X ---------------------------- X | |

AEs = adverse events; CBC = complete blood count; IgG = immunoglobulin G; MCV4 = meningococcal polysaccharide diphtheria conjugate vaccine (quadrivalent); PPSV23 = 23-valent pneumococcal polysaccharide vaccine; SAEs = serious adverse events; Td = tetanus diphtheria toxoids vaccine.
[1]Written informed consent will be obtained prior to performing any study-related procedures.
[2]Vital signs will include height (measured at Screening only), weight, diastolic and systolic blood pressure, heart rate, and temperature. Subjects will be seated for 5 minutes prior to having their pulse and blood pressure measured.
[3]Blood samples will be collected prior to vaccine administration.
[4]Females of childbearing potential only. Results will be known to be negative prior to vaccine administration.
[5]Subjects will be observed in the clinic for at least 30 minutes following their final vaccine administration.

5.2.4 Study Objectives and Endpoints 5.2.4.1. Objectives

Primary Objective

The primary objective of the study is to evaluate the immune response to vaccination with Td in subjects with relapsing forms of MS who have been treated with Tecfidera versus those treated with non pegylated IFN.

Secondary Objective

The secondary objective of the study is to evaluate the immune response to vaccination with PPSV23 and MCV4.

5.2.4.2. Endpoints

Primary Endpoint

The proportion of subjects with a ≥2-fold rise in anti tetanus serum immunoglobulin G (IgG) levels from pre-vaccination to 4 weeks after Td vaccination.

Secondary Endpoints

The proportion of subjects with a ≥4 fold rise in anti tetanus serum IgG levels from pre vaccination to 4 weeks after Td vaccination.

The proportion of subjects with a ≥2-fold and a ≥4-fold rise in anti pneumococcal serum IgG levels against serotypes 3 and 8 from pre vaccination to 4 weeks after PPSV23 vaccination.

The proportion of subjects with a ≥2-fold and a ≥4-fold rise in anti meningococcal serum IgG levels against serotype C from pre-vaccination to 4 weeks after MCV4 vaccination.

The geometric mean titer ratios from pre-vaccination to 4 weeks after Td, PPSV23, and MCV4 vaccinations.

Incidence of adverse events (AEs) and serious adverse events (SAEs).

Clinical laboratory shifts in reported values.

Clinically significant changes in vital sign measurements.

Exploratory Endpoints

The proportion of subjects with a ≥2-fold and a ≥4-fold rise in anti-diphtheria toxoid serum IgG levels from pre-vaccination to 4 weeks after MCV4 vaccination.

The anti-diphtheria geometric mean titer ratio from pre-vaccination to 4 weeks after MCV4 vaccination.

The proportion of subjects with anti-tetanus and anti-meningococcal serprotective levels at 4 weeks after Td and MCV4 vaccinations.

5.2.5 Study Design 5.2.5.1. Study Overview

This is an open-label, multicenter study to evaluate the immune response to vaccination in subjects with relapsing forms of MS who have been treated for at least 6 months with the approved dose of Tecfidera (240 mg BID) or who have been treated for at least 3 months with an approved dose of a non pegylated IFN (e.g., Avonex, Betaseron, Rebif, Extavia). This study will be conducted at approximately 10 to 15 sites in the US.

After a 28-day Screening Period, approximately 70 eligible subjects will be enrolled and assigned as appropriate into either Group 1 (currently treated with Tecfidera) or Group 2 (currently treated with non-pegylated IFN), with approximately 35 subjects in each group.

Throughout the study, subjects will remain on their existing, stable dosing regimen of Tecfidera or non pegylated IFN.

Subjects will come to the clinic on Day 1 and have blood samples drawn for pre-vaccination anti-tetanus, anti pneumococcal, anti meningococcal, and anti diphtheria IgG titers. All subjects will receive 3 vaccinations: Td, PPSV23, and MCV4. They will return to the clinic at Week 4 for their final study visit, at which time blood samples will be drawn for post-vaccination IgG titers.

Subjects who receive at least 1 dose of a vaccine should remain in the study and attend the Week 4 Visit. Subjects who receive at least 1 dose of a vaccine but would like to withdraw from the study prematurely will be asked to return to the clinic for an Early Withdrawal Visit, at which time blood samples will be drawn for IgG titers.

Safety evaluations in this study will include blood samples for complete blood count with differential and blood chemistry, urine pregnancy tests, and vital signs at Day 1 and Week 4, as well as ongoing collection of AEs, SAEs, and concomitant medications as detailed in Table 3: Schedule of Events.

The subjects' neurologist or primary healthcare provider will manage their MS care before, during, and after study participation.

5.2.5.2. Overall Study Duration and Order of Study Procedures

In both groups, subjects will have 3 clinic visits: Screening, Day 1, and Week 4. The duration of study participation will be approximately 8 weeks. The following sections outline the timing and order of procedures conducted at each study visit. The procedures are listed in the order of preferred collection by the Sponsor to enhance data clarity. Altering the order is not considered a protocol deviation with the exception of the timing of blood collection in relation to vaccination (i.e., blood samples for pre-vaccination titers will be collected before vaccinations are given) and the order of vaccine administration.

5.2.5.3. Screening Visit

Subjects will be screened and meet eligibility criteria for the study within 28 days prior to study entry.

At the Screening Visit, informed consent will be given before any screening activities are conducted. Other procedures to be conducted during the Screening Visit, in preferred order, are listed below:
Concomitant therapy and procedure recording
Medical history
Vital signs
Physical examination
Review of inclusion/exclusion criteria (except laboratory results)
Collection of blood samples for anti-tetanus IgG titer, hematology, blood chemistry, and serum pregnancy test
AE assessment and reporting

5.2.5.4. Day 1 Visit

Subjects who pass screening will return to the clinic for the Day 1 Visit.

At the Day 1 Visit, the following procedures will be completed before study vaccines are administered and are listed in preferred order:
AE and SAE assessment and recording
Concomitant therapy and procedure recording
Review of inclusion/exclusion criteria
Urine pregnancy test (females only)—do not vaccinate subject unless pregnancy has been excluded with a negative pregnancy test
Vital signs
Collection of blood samples for anti-tetanus, anti-pneumococcal, anti meningococcal, and anti-diphtheria IgG titers; hematology; and blood chemistry
After completing these assessments, study vaccines will be administered in the following order:
1. Td
2. PPSV23
3. MCV4
Subjects will remain at the clinic for at least 30 minutes after their final vaccination for observation.

5.2.5.5. Week 4/Early Withdrawal Visit

Subjects in both groups will have a clinic visit 4 weeks after vaccination. Subjects who have received at least 1 vaccination but withdraw prematurely from the study will be asked to return to the clinic for an Early Withdrawal Visit.

Procedures to be conducted during the Week 4/Early Withdrawal Visit, in preferred order, are listed below:
AE and SAE assessment and recording
Concomitant therapy and procedure recording
Urine pregnancy test (females only)
Vital signs
Collection of blood samples for anti-tetanus, anti-pneumococcal, anti meningococcal, and anti-diphtheria IgG titers; hematology; and blood chemistry

5.2.5.6. End of Study

The end of study is last subject, last visit for final collection of data.

5.2.6 Selection of Subjects

5.2.6.1. Inclusion Criteria

Unless otherwise specified, to be eligible to participate in this study, candidates will meet the following eligibility criteria at Screening and on Day 1 or at the timepoint specified in the individual eligibility criterion:
1. Ability to understand the purpose and risks of the study and provide signed and dated informed consent and authorization to use protected health information (PHI) in accordance with national and local subject privacy regulations.
2. Aged 18 to 55 years old, inclusive, at the time of informed consent.
3. Women of childbearing potential will practice appropriate contraception (per the local Tecfidera or non-pegylated IFN prescribing information) as determined by the Investigator.
4. Will have a confirmed diagnosis of RRMS per the 2010 McDonald criteria [Polman 2011].
5. Will have a known tetanus immunization history with most recent tetanus vaccination given 2 to 15 years prior to Screening and an anti-tetanus IgG titer at Screening that is less than or equal to one-half the upper limit of detection for the assay.
6. Will have been on a stable approved dose of Tecfidera (240 mg BID) [Group 1] for ≥6 months or on a stable approved dose of a non-pegylated IFN (e.g., Avonex, Betaseron, Rebif, Extavia) [Group 2] for ≥3 months prior to Day 1.

Note: Subjects will have received their MS treatment as monotherapy for the required duration, except during treatment of relapses.

5.2.6.2. Exclusion Criteria

Unless otherwise specified, candidates will be excluded from study entry if any of the following exclusion criteria exist at Screening and on Day 1 or at the timepoint specified in the individual eligibility criterion:
Medical History
1. Clinical relapse requiring treatment within 30 days prior to Day 1.
2. Pneumococcal vaccination within 5 years prior to Screening.
3. Previous exposure to meningococcal vaccines.
4. Known hypersensitivity to Td, PPSV23, or MCV4 or their components.
5. History of hepatitis C or hepatitis B virus.

6. History of human immunodeficiency virus.
7. History of drug or alcohol abuse (as defined by the Investigator) within 2 years prior to Screening.
8. Current smoker or smoking within 6 months prior to Screening.
9. Any clinically significant infectious illness (e.g., cellulitis, abscess, pneumonia, septicemia) within 30 days prior to Screening.
10. Any active bacterial or viral infection or an oral temperature ≥38.0° C./100.4° F. on Day 1 or within 3 days prior to Day 1. Subjects with a clinically significant active infection or measured oral (sublingual) temperature ≥38.0° C./100.4° F. should have vaccinations postponed until the subject's temperature remains below 38.0° C./100.4° F. for at least 3 days and the subject's acute illness has resolved.
11. History of clinically significant cardiovascular, dermatologic, endocrinologic, gastrointestinal, hematologic, hepatic, immunologic, metabolic, neurologic (other than MS), psychiatric, pulmonary, renal, urologic, and/or other major disease that may confound safety or efficacy assessments.
12. History of malignancy (subjects with basal cell carcinoma that has been completely excised prior to study entry remain eligible).
13. History of severe allergic reactions, anaphylactic reactions, or known drug hypersensitivity to Tecfidera or fumaric acid esters.
14. Any abnormal laboratory assessment judged to be clinically significant by the Investigator at Screening.
Note: The following analytes are strictly exclusionary:
leukocytes <2500/mm³
lymphocytes <500/mm³
alanine transaminase or aspartate transaminase >2 times the upper limit of normal
Treatment History
15. Any type of vaccine, with the exception of inactivated influenza vaccination (the flu shot), within 4 weeks prior to Day 1 (the inactivated flu shot is allowed; the intranasal live vaccine is not allowed).
16. Prior treatment with any of the following:
    cladribine
    mitoxantrone
    fingolimod
    total lymphoid irradiation
    T-cell or T-cell-receptor vaccination
    any therapeutic monoclonal antibody, with the exception of Tysabri● (natalizumab)(see exclusion #17).
17. Prior treatment with Tysabri (natalizumab) within 1 year prior to Screening.
18. Prior treatment with any of the following medications or procedures within 6 months prior to Screening:
    cyclosporine
    azathioprine
    methotrexate
    mycophenolate mofetil
    intravenous immunoglobulin
    plasmapheresis or cytapheresis
    subcutaneous or oral glatiramer acetate
19. Treatment with any immunosuppressive drug or regimen within 3 months prior to Day 1, including but not limited to chronic steroid use (defined as continuous [>14 days] use of intravenous or oral corticosteroid treatment, with a dosage equivalence of >20 mg/day of oral prednisone) or agents that may act through the corticosteroid pathway (e.g., low dose naltrexone).
20. Treatment with any investigational drug or approved therapy for investigational use within the 6 months prior to Day 1 or during the study.
Miscellaneous
21. Female subjects who are currently pregnant or breast-feeding or planning to become pregnant while in the study.
22. Current enrollment in any other investigational study within 6 months prior to Day 1.
    Note: Current enrollment in an observational study that docs not involve drugs, vaccines, or medical devices is allowed.
23. Unwillingness or inability to comply with the requirements of the protocol including the presence of any condition (physical, mental, or social) that is likely to affect the subject's ability to comply with the protocol.
24. Any other reasons that, in the opinion of the Investigator and/or the Sponsor, the subject is determined to be unsuitable for enrollment in this study.

5.2.7 Treatment of Subjects 5.2.7.1. Vaccinations

On Day 1, following all other assessments, subjects in both groups will receive the following vaccinations intramuscularly in the specified order:
1. Td (Tenivac●, 0.5 mL)
2. PPSV23 (Pneumovax● 23, 0.5 mL)
3. MCV4 (Menveo●, 0.5 mL)

5.2.7.2. Concomitant Therapy

A concomitant therapy is any drug or substance administered from the time the subject is enrolled in the study until the subject's final study visit.

5.2.7.3. Disallowed Concomitant Therapy

Concomitant therapy with any of the following is not allowed, unless approved by the Medical Monitor, or as otherwise described in this protocol:
    Any treatment for MS, such as chronic immunosuppressant therapy or other immunomodulatory treatments (including, but not limited to: glatiramer acetate, natalizumab, cyclophosphamide, methotrexate, azathioprine, fingolimod, alemturumab, teriflunomide, or related products, etc.), with the exception of treatments required as a condition for study eligibility and treatments for acute management of relapses.
    Any investigational product, including investigational symptomatic therapies for MS and investigational therapies or vaccines for non-MS indications.
    Any systemic steroid therapy including, but not limited to, oral corticosteroids (e.g., prednisone) or periodic (e.g., monthly) treatment with intravenous methylprednisolone, except for treatment of a relapse. Steroids that am administered by nonsystemic routes (e.g., topical, inhaled) are allowed.
    Total lymphoid irradiation, cladribine, T-cell or T-cell-receptor vaccination, any therapeutic monoclonal antibody, mitoxantrone, cyclosporine, intravenous immunoglobulin, plasmapheresis, or cytapheresis.
    Live or live-attenuated vaccines.
Subjects should be instructed not to start taking any new medications, including nonprescribed drugs, unless they have received permission from the Investigator.

5.2.7.4. Concomitant Procedures

A concomitant procedure is any therapeutic intervention (e.g. surgery/biopsy, physical therapy) or diagnostic assessment (e.g., blood gas measurement, bacterial cultures) performed between the time the subject is enrolled in the study until the subject's final study visit.

The use of concomitant therapies or procedures defined above will be recorded on the subject's case report form (CRF), according to instructions for CRP completion. AEs related to administration of these therapies or procedures will be documented on the appropriate CRF.

5.2.8 Efficacy Assessments

Blood samples will be collected for anti-tetanus, anti pneumococcal, anti meningococcal, and anti-diphtheria IgG titers before vaccination on Day 1 and after vaccination at Week 4 or the Early Withdrawal Visit.

Refer to Table 3: Schedule of Events, for the timing of assessments.

5.2.9 Safety Assessments

5.2.9.1. Clinical Safety Assessments

The following clinical assessments will be performed during the study:
- Vital sign measurements
- Physical examination
- Monitoring/recording of AEs
- Monitoring/recording of concomitant therapy and procedures Refer to Table 3: Schedule of Events, for the timing of assessments.

5.2.9.2. Laboratory Safety Assessments

The following laboratory tests will be performed during the study:
- Hematology: hemoglobin, hematocrit, red blood cell count, white blood cell count (with differential), and platelet count
- Blood chemistry: sodium, potassium, chloride, total bilirubin, alanine transaminase, aspartate transaminase, gamma glutamyl transferase, blood urea nitrogen, and creatinine
- Urine and serum pregnancy tests Refer to Table 3: Schedule of Events, for the timing of assessments.

5.2.10 References for Example 2

Olberg H K, Cox R J, Nostbakken J K, et al. Immunotherapies influence the influenza vaccination response in multiple sclerosis patients: an explorative study. Mult Scler. 2014; 20(8):1074-1080.

Polman C H, Reingold S C, Banwell B, et al. Diagnostic criteria for multiple sclerosis: 2010 Revisions to the McDonald criteria. Ann Neurol. 2011; 69(2):292-302.

Schwid S R, Thorpe J, Sharief M, et al. Enhanced benefit of increasing interferon beta-1a dose and frequency in relapsing multiple sclerosis: the EVIDENCE Study. Arch Neurol. 2005; 62(5):785-92.

6. INCORPORATION BY REFERENCE

Various references such as patents, patent applications, and publications are cited herein, the disclosures of which are hereby incorporated by reference herein in their entireties.

What is claimed is:

1. A method of treating multiple sclerosis in a human subject in need thereof, said method comprising:
    (a) administering to the subject a first dose of a pharmaceutical composition for a first dosing period, wherein the pharmaceutical composition comprises a fumarate agent selected from the group consisting of monomethyl fumarate, a pharmaceutically acceptable salt of monomethyl fumarate, dimethyl fumarate, and a combination thereof;
    (b) administering a vaccine to the subject, wherein the subject receives the vaccine during the first dosing period; and
    (c) administering to the subject a second dose of the pharmaceutical composition for a second dosing period, wherein: (i) the second dosing period is after the first dosing period, and (ii) the second dosing period is initiated within one day of the end of the first dosing period;
    wherein the second dose is the same as the first dose, and the first dose and the second dose are administered daily;
    wherein the multiple sclerosis is a relapsing form of multiple sclerosis;
    wherein the vaccine is an inactive vaccine;
    wherein the first dose is a therapeutically effective amount of monomethyl fumarate, a pharmaceutically acceptable salt of monomethyl fumarate, dimethyl fumarate, or a combination thereof; and
    wherein the method further comprises 10 minutes to an hour before said administering step (a), or 10 minutes to an hour before said administering step (c), a step of administering to the subject a non-steroidal anti-inflammatory drug.

2. The method of claim 1, wherein the fumarate agent is dimethyl fumarate.

3. The method of claim 2, wherein the first dose is a daily amount of about 480 mg dimethyl fumarate.

4. The method of claim 1, further comprising administering a titration dose of the fumarate agent prior to the first dosing period.

5. The method of claim 4, wherein the fumarate agent is dimethyl fumarate and the titration dose is a daily amount of about 240 mg dimethyl fumarate.

6. The method of claim 1, wherein the pharmaceutical composition is in the form of a capsule or tablet.

7. The method of claim 2, wherein the dimethyl fumarate is in the form of microtablets or micropellets, and wherein the microtablets or micropellets are enterically coated.

8. The method of claim 7 wherein the microtablets or micropellets are contained in a capsule.

9. The method of claim 1, wherein the vaccine induces a T cell-dependent immune response.

10. The method of claim 9, wherein the vaccine induces a T cell-dependent anamnestic humoral immune response.

11. The method of claim 9, wherein the vaccine induces a T cell-dependent neoantigen immune response.

12. The method of claim 1, wherein the vaccine induces a T cell-independent immune response.

13. The method of claim 1, wherein the vaccine is a vaccine selected from the group consisting of tetanus diphtheria toxoids vaccine, keyhole limpet hemocyanin vaccine, pneumovax-23 vaccine, and a combination thereof.

14. The method of claim 13, wherein the vaccine is tetanus diphtheria toxoids vaccine.

15. The method of claim 13, wherein the vaccine is keyhole limpet hemocyanin vaccine.

16. The method of claim 13, wherein the vaccine is pneumovax-23 vaccine.

17. The method of claim 1, wherein the vaccine is meningococcal polysaccharide diphtheria conjugate vaccine quadrivalent.

18. The method of claim 1, wherein the multiple sclerosis is relapsing-remitting multiple sclerosis.

19. The method of claim 1, wherein the multiple sclerosis is secondary progressive multiple sclerosis.

20. The method of claim 3, further comprising administering a titration dose of the fumarate agent prior to the first dosing period.

21. The method of claim 20, wherein the titration dose is a daily amount of about 240 mg dimethyl fumarate.

22. The method of claim 1, wherein the fumarate agent is monomethyl fumarate.

23. The method of claim 1, wherein the fumarate agent is a pharmaceutically acceptable salt of monomethyl fumarate.

24. The method of claim 1, wherein the non-steroidal anti-inflammatory drug is selected from the group consisting of aspirin, ibuprofen, naproxen, ketoprofen, celecoxib, and a combination thereof.

25. The method of claim 24, wherein the non-steroidal anti-inflammatory drug is aspirin.

26. The method of claim 25, wherein the aspirin is administered 30 minutes before said administering step (a), or 30 minutes before said administering step (c).

* * * * *